(12) United States Patent
Di Resta et al.

(10) Patent No.: US 10,357,191 B2
(45) Date of Patent: Jul. 23, 2019

(54) CONTINUOUS GLUCOSE MONITORING ON-BODY SENSOR

(71) Applicant: Becton, Dickinson and Company, Franklin Lakes, NJ (US)

(72) Inventors: Ellen Di Resta, Arlington, MA (US); John Prudden, Manchester, MA (US); James Salemme, Billerica, MA (US); Jack Gundlach, Acton, MA (US); Ann Sullivan Treacy, South Yarmouth, MA (US); Jennifer Linnane, Melrose, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 984 days.

(21) Appl. No.: 14/775,693

(22) PCT Filed: Mar. 10, 2014

(86) PCT No.: PCT/US2014/022637
§ 371 (c)(1),
(2) Date: Sep. 12, 2015

(87) PCT Pub. No.: WO2014/159235
PCT Pub. Date: Oct. 2, 2014

(65) Prior Publication Data
US 2016/0022179 A1 Jan. 28, 2016

Related U.S. Application Data

(60) Provisional application No. 61/782,148, filed on Mar. 14, 2013.

(51) Int. Cl.
| A61B 5/1459 | (2006.01) |
| A61B 5/00 | (2006.01) |
| A61B 5/145 | (2006.01) |

(52) U.S. Cl.
CPC ........ *A61B 5/1459* (2013.01); *A61B 5/14532* (2013.01); *A61B 5/6832* (2013.01); *A61B 5/6833* (2013.01); *A61B 5/6848* (2013.01)

(58) Field of Classification Search
CPC ... A61B 5/1477; A61B 5/1455; A61B 5/1459; A61B 5/14532; A61B 5/6832; A61B 5/6848; A61B 5/68335
See application file for complete search history.

(56) References Cited

U.S. PATENT DOCUMENTS

| 3,675,766 A | 7/1972 | Rosenthal |
| 5,299,571 A | 4/1994 | Mastrototaro |

(Continued)

FOREIGN PATENT DOCUMENTS

| CN | 101558992 A | 10/2009 |
| EP | 1185202 A2 | 3/2002 |

(Continued)

OTHER PUBLICATIONS

Medtronic, "A Practical Guide to Continuous Glucose Monitoring." Dec. 2011, pp. 11-12 [online]. Retrieved on Jun. 21, 2014 from http://www.medtronic-diabetes.com.au/wcm/groups/mdtcom_sg/@mdt/@ap/@au/@diabetes/documents/documents/contrib_107974.pdf.

*Primary Examiner* — Eric F Winakur
(74) *Attorney, Agent, or Firm* — Dickinson Wright, PLLC

(57) ABSTRACT

An on-body sensor (OBS) (5610) having a continuous monitoring (CGM) device is disclosed for use in identifying an analyte, such as glucose in blood or interstitial fluid (ISF), using a biomaterial, such as glucose binding protein (GBP), that is brought into contact with the analyte. The on-body sensor (5610) incorporating the CGM device includes a housing (5625') which provides protection to the CGM device while providing comfort to a user wearing the device.

(Continued)

The OBS also includes an adhesive structure that provides a comfortable, discreet and secure user experience.

68 Claims, 43 Drawing Sheets

(56) References Cited

U.S. PATENT DOCUMENTS

| | | |
|---|---|---|
| 5,954,643 A | 9/1999 | Vanantwerp et al. |
| 6,845,272 B1 | 1/2005 | Thomsen et al. |
| 2006/0258959 A1 | 11/2006 | Sode |
| 2007/0073129 A1 | 3/2007 | Shah et al. |
| 2007/0135698 A1 | 6/2007 | Shah et al. |
| 2010/0305416 A1 | 12/2010 | Bedard et al. |
| 2011/0060196 A1 | 3/2011 | Stafford |
| 2011/0077490 A1 | 3/2011 | Simpson et al. |
| 2011/0144470 A1 | 6/2011 | Mazar et al. |
| 2012/0071731 A1 | 3/2012 | Gottesman |
| 2012/0310070 A1 | 12/2012 | Kumar et al. |

FOREIGN PATENT DOCUMENTS

| | | |
|---|---|---|
| JP | 2002-191582 | 7/2002 |
| JP | 2002-306486 | 10/2002 |
| JP | 2004-313269 | 11/2004 |
| JP | 2008-539810 A | 11/2008 |
| WO | WO-0076575 A2 | 12/2000 |
| WO | WO-2007/037989 A2 | 4/2007 |
| WO | WO-2009/107135 A2 | 9/2009 |
| WO | WO-2010111788 A1 | 10/2010 |
| WO | WO-2012/067115 A1 | 5/2012 |

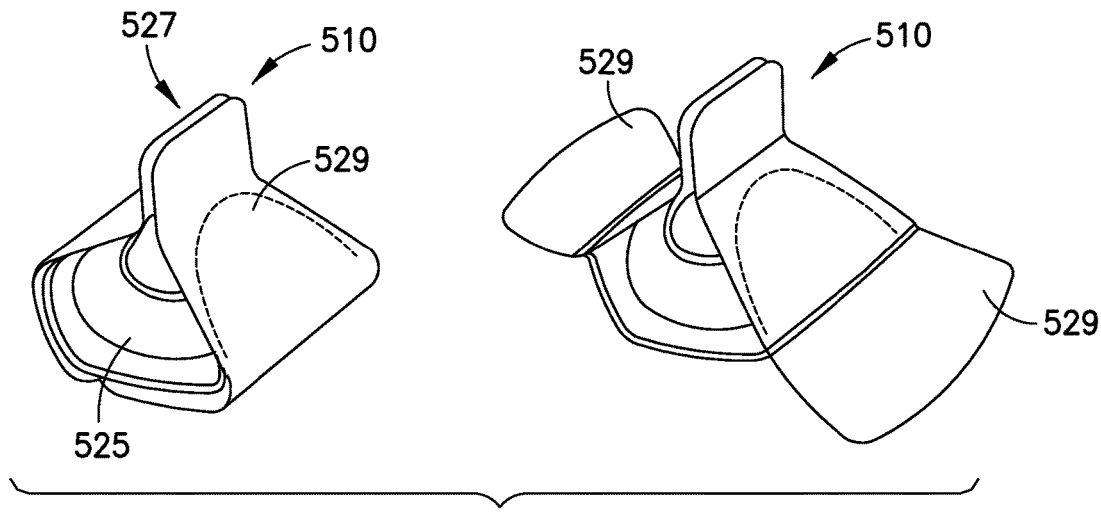
FIG.5
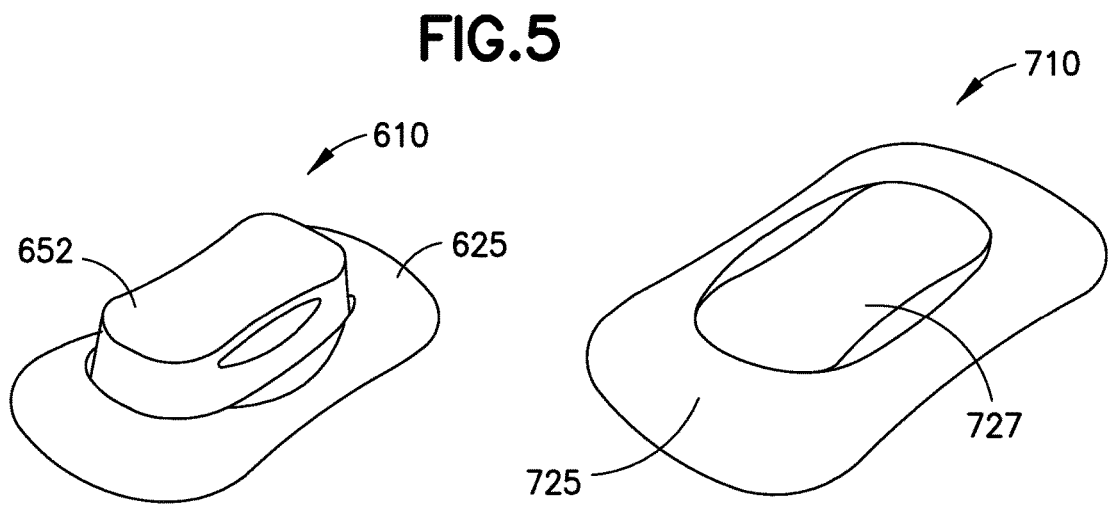
FIG.6
FIG.7
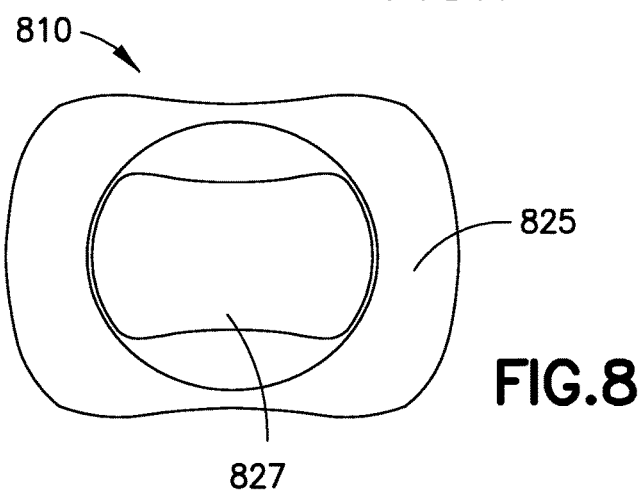
FIG.8

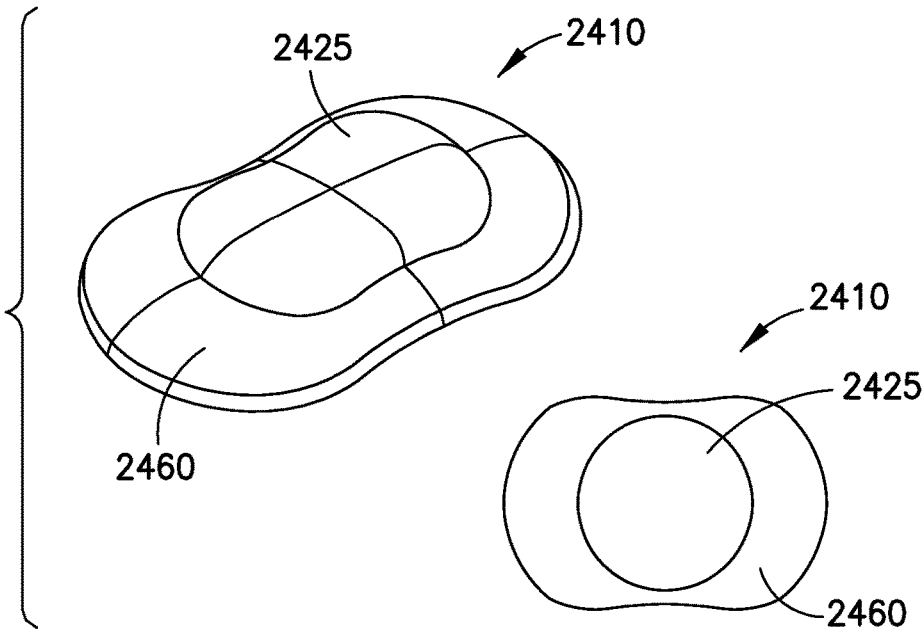
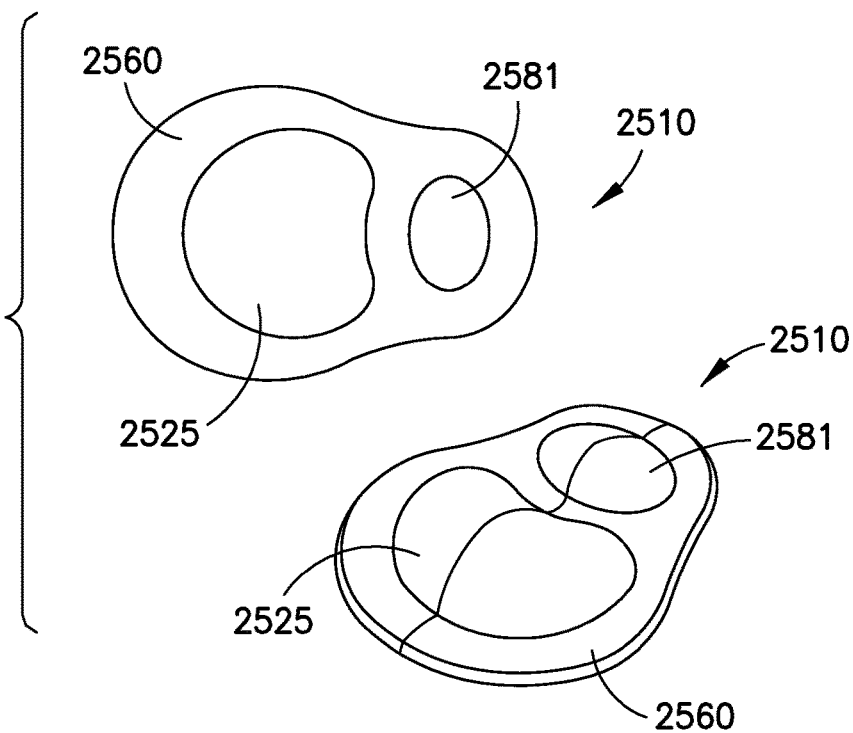

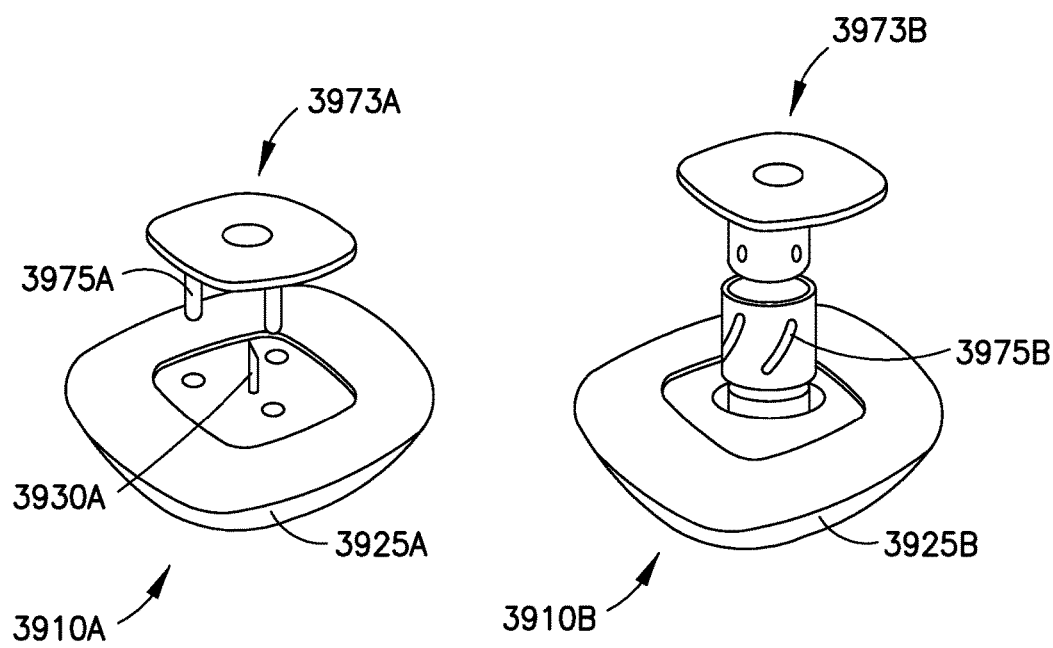
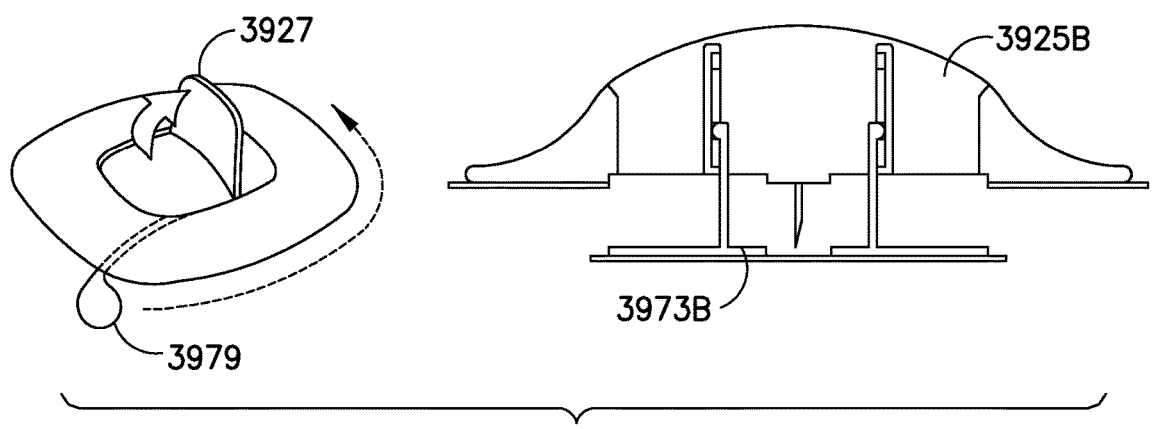
FIG.39

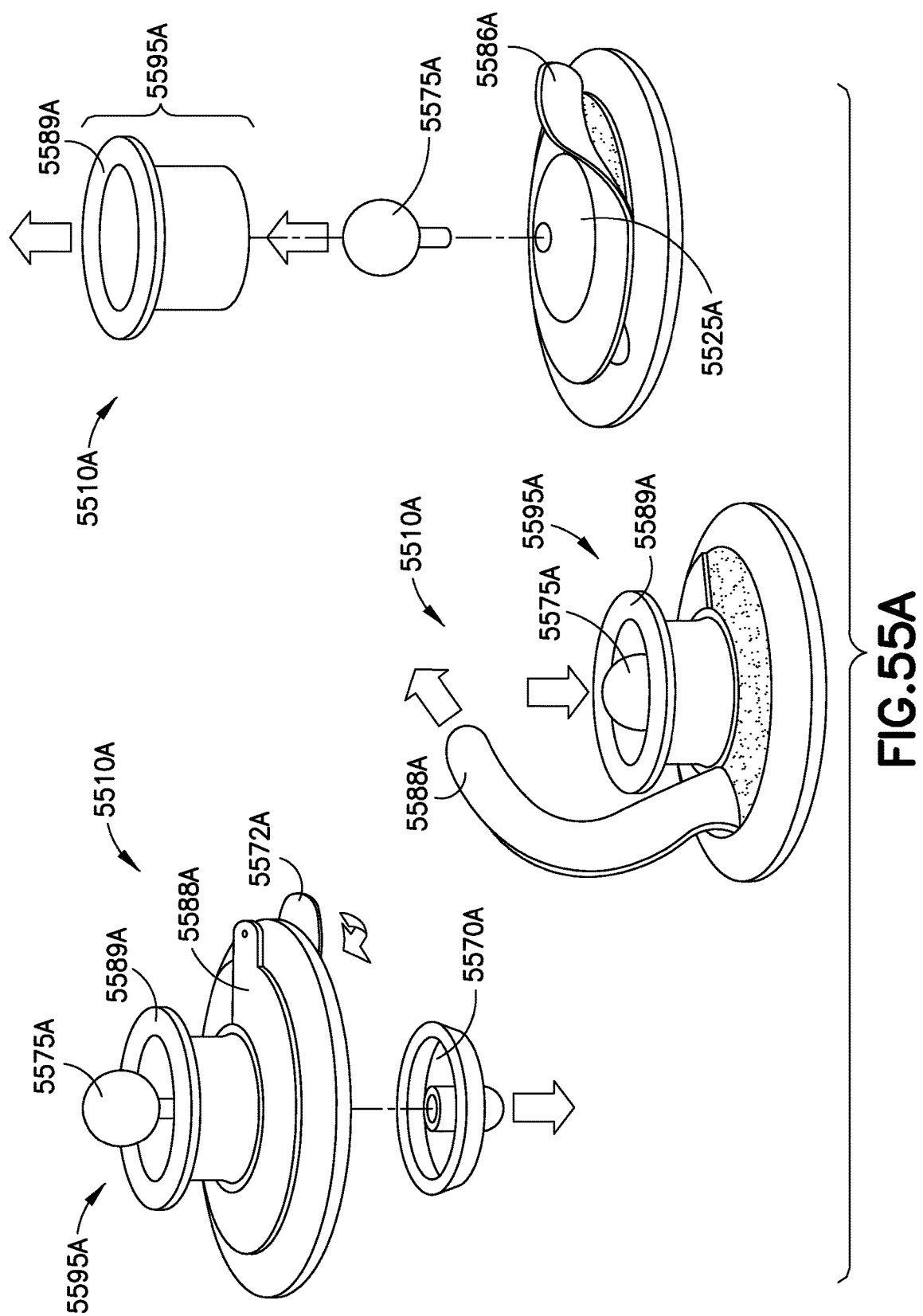

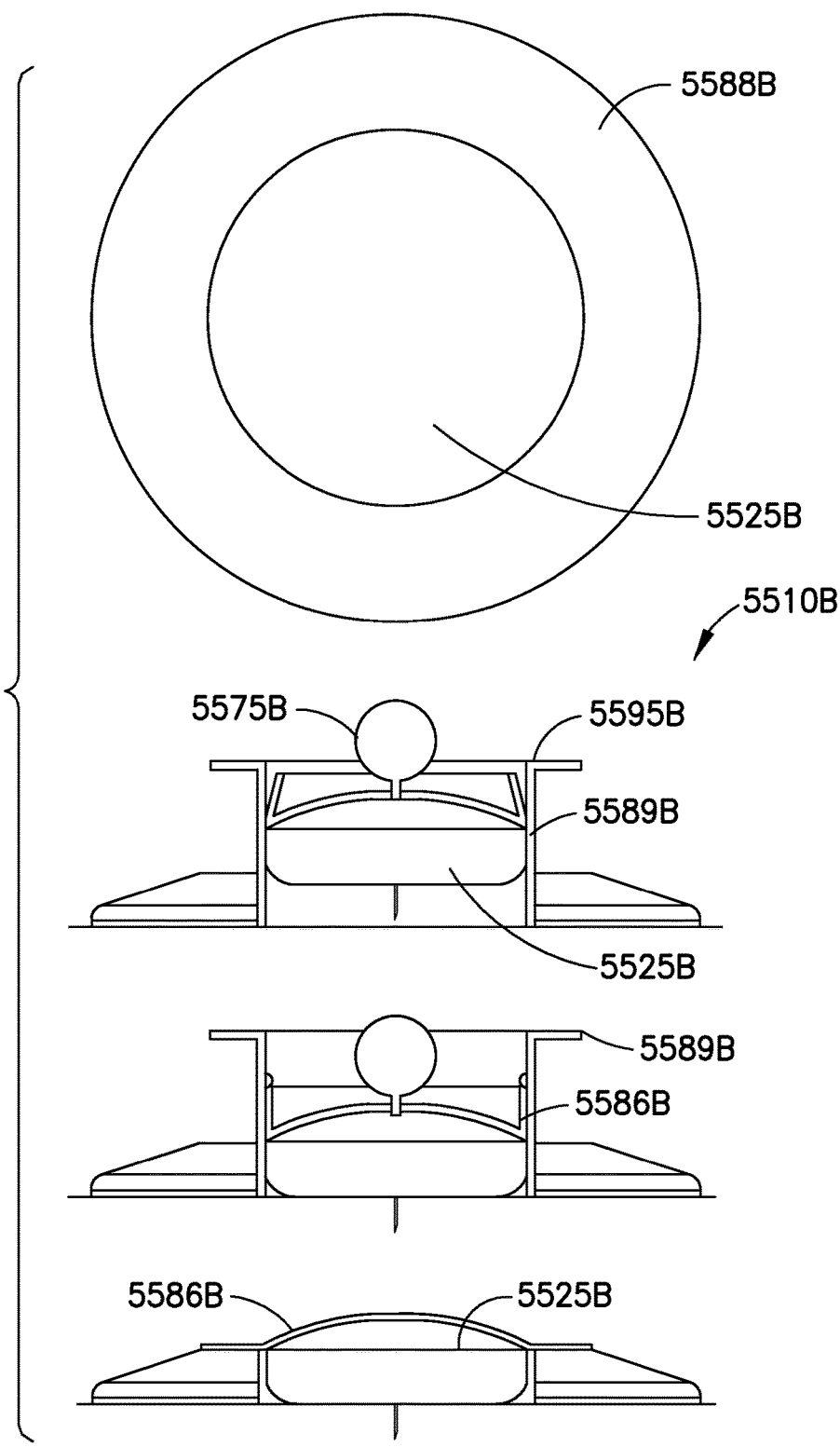

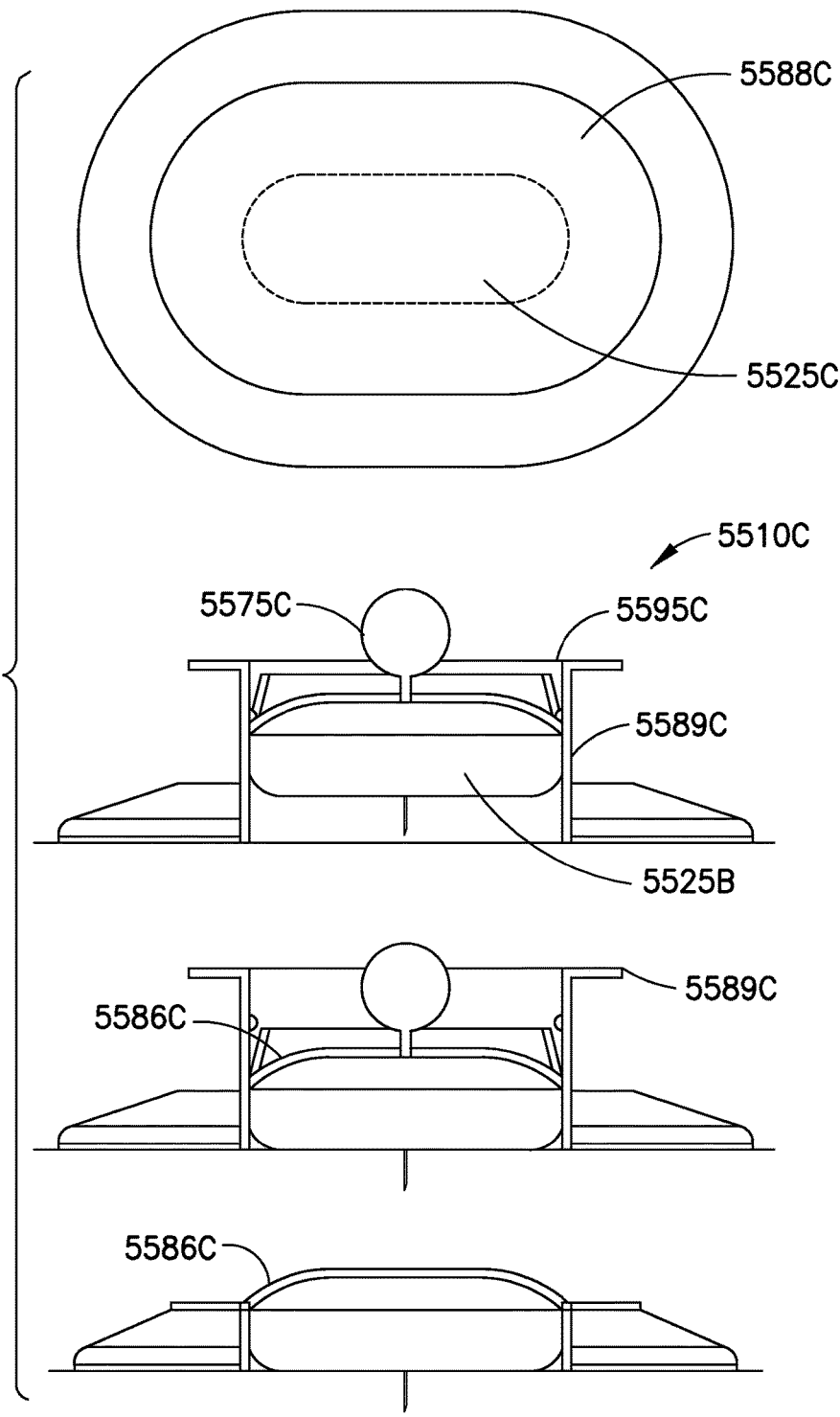

CONTINUOUS GLUCOSE MONITORING ON-BODY SENSOR

CROSS-REFERENCE TO RELATED APPLICATION

This application claims the benefit under 35 U.S.C. § 119 (e) of U.S. Provisional Application No. 61/782,148, filed on Mar. 14, 2013, in the U.S. Patent and Trademark Office, the entire disclosure of which is incorporated herein by reference.

FIELD OF THE INVENTION

The present invention relates generally to continuous glucose monitoring (CGM) devices used to continuously monitor subcutaneous glucose using optical interrogation of a glucose binding protein (GBP) to determine the concentration of glucose in a user. More particularly, the present invention relates to on-body sensors (OBS) incorporating CGM devices, the OBS having external housings and adhesive structures that provide a comfortable, discreet and secure user experience.

BACKGROUND OF THE INVENTION

In patients with diabetes, glucose levels need to be monitored to maintain a healthy balance of glucose in the body. Glucose levels can be monitored by GBP coated sensors such as on-body CGM devices. CGM devices typically have glucose sensors including a needle or probe that is inserted into the tissue of a user to measure the glucose levels in the surrounding tissue fluid.

Conventionally, on-body CGM devices are usually small and configured to be secured to the skin of a user's abdomen during each sensor wear period. A transmitter is incorporated into the CGM device and communicates with a handheld receiver. The data collected by the CGM device is transferred to the receiver at intervals throughout the wear period.

However, many problems often arise when users must wear the on-body CGM device for an extended period of time. For example, on-body CGM devices have caused skin redness, rash, bruises, bleeding, tape irritation, blistering and edema.

Normal body movement of a user can also cause unwanted micro-motion of the needle or probe which can compromise the data collected by the CGM device. Additionally, the shape and exterior configuration of the on-body CGM device can catch on a user's clothing causing additional irritation to the user and even malfunction of the device itself.

SUMMARY OF THE INVENTION

An object of illustrative embodiments of the present invention is to substantially address the above and other concerns, and provide improved structure and other advantages to OBS devices.

Another object of illustrative embodiments of the present invention is to provide an OBS device that will increase patient satisfaction as it pertains to comfort of the device.

Another object of illustrative embodiments of the present invention is to allow a patient to move freely while maintaining the proper positioning of the OBS device.

Another object of illustrative embodiments of the present invention is to enable the OBS device to flex and move with the user, but reduce micro-motions of the needle that can cause malfunction of the OBS and injure the user.

Another object of illustrative embodiments of the present invention is to house the electronics components of the OBS in a hard cover for protection and include a soft bumper over-layer for increased comfort to the user.

Another object of illustrative embodiments of the present invention is to reduce the overall size and profile of the OBS device to reduce skin irritation and nuisance to the user.

These and other objects are substantially achieved by providing an illustrative on-body CGM sensor device wherein the device includes a cover having a reduced profile and increased flexibility while maintaining structural and positional integrity, thereby improving the comfort, durability and securement of the device.

BRIEF DESCRIPTION OF THE DRAWINGS

The various objects, advantages and novel features of the illustrative embodiments of the present invention will be more readily appreciated from the following detailed description when read in conjunction with the appended drawings, in which:

FIG. 5 shows another illustrative embodiment of an OBS device in accordance with the present invention, having an adhesive release paper with opposing flaps;

FIG. 6 shows another illustrative embodiment of an OBS device in accordance with the present invention, having a needle inserter;

FIG. 7 shows another illustrative embodiment of an OBS device in accordance with the present invention, having an integrated handle;

FIG. 8 shows another illustrative embodiment of an OBS device in accordance with the present invention, having a cover and a handle with an hourglass-like shape;

FIG. 24 shows another illustrative embodiment of an OBS device in accordance with the present invention, having a compound curved-shaped flange;

FIG. 25 shows another illustrative embodiment of an OBS device in accordance with the present invention, having a separate battery pod;

FIG. 39 shows another illustrative embodiment of an OBS device in accordance with the present invention, having a cover configured to receive a stabilizer;

FIGS. 55A-55C shows other illustrative embodiments of an OBS device in accordance with the present invention, having an applicator assembly;

DETAILED DESCRIPTION OF ILLUSTRATIVE EMBODIMENTS

Figure 1:
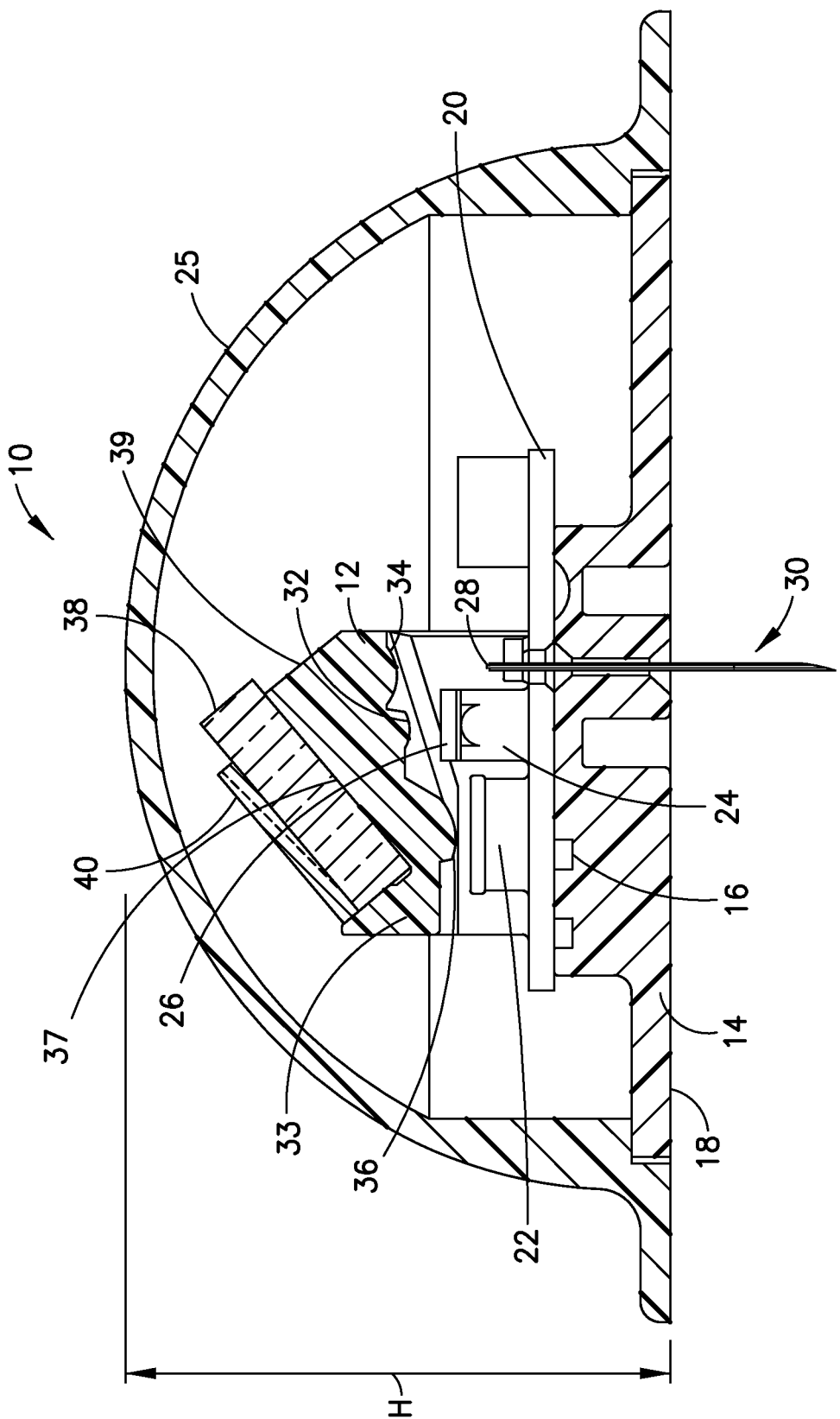
FIG. 1 is a cross-sectional view of a CGM device in accordance with an illustrative embodiment of the present invention.

As will be appreciated by one skilled in the art, there are numerous ways of carrying out the examples, improvements and arrangements of on-body CGM sensors disclosed herein. Although reference will be made to the illustrative embodiments depicted in the drawings and the following descriptions, the embodiments disclosed herein are not meant to be exhaustive of the various alternative designs and embodiments that are encompassed by the disclosed invention.

Figure 2:
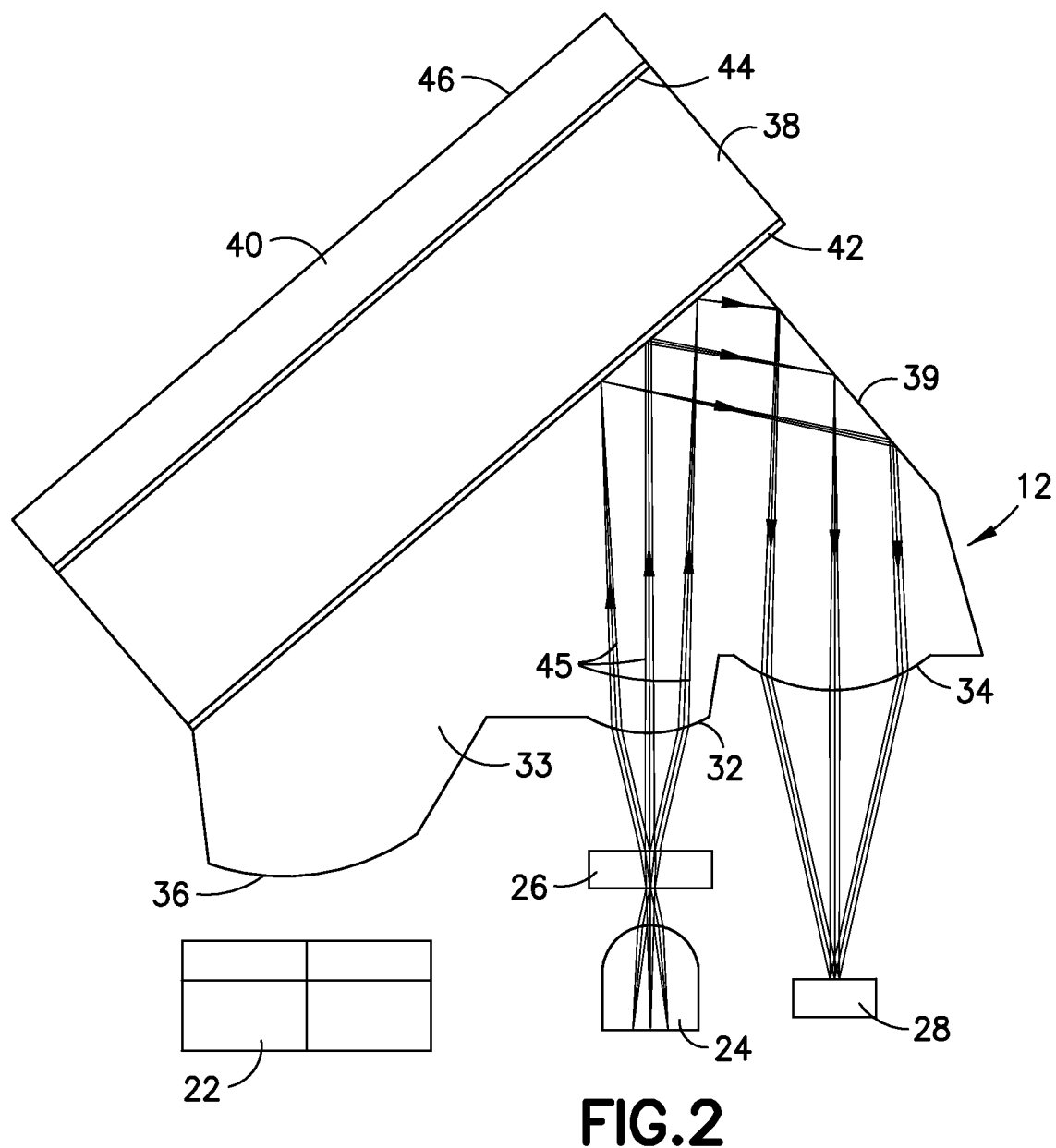
FIG. 2 is a schematic diagram of the CGM device of FIG. 1 including ray traces through an optical coupler, from an LED to a fiber face.
Figure 3:
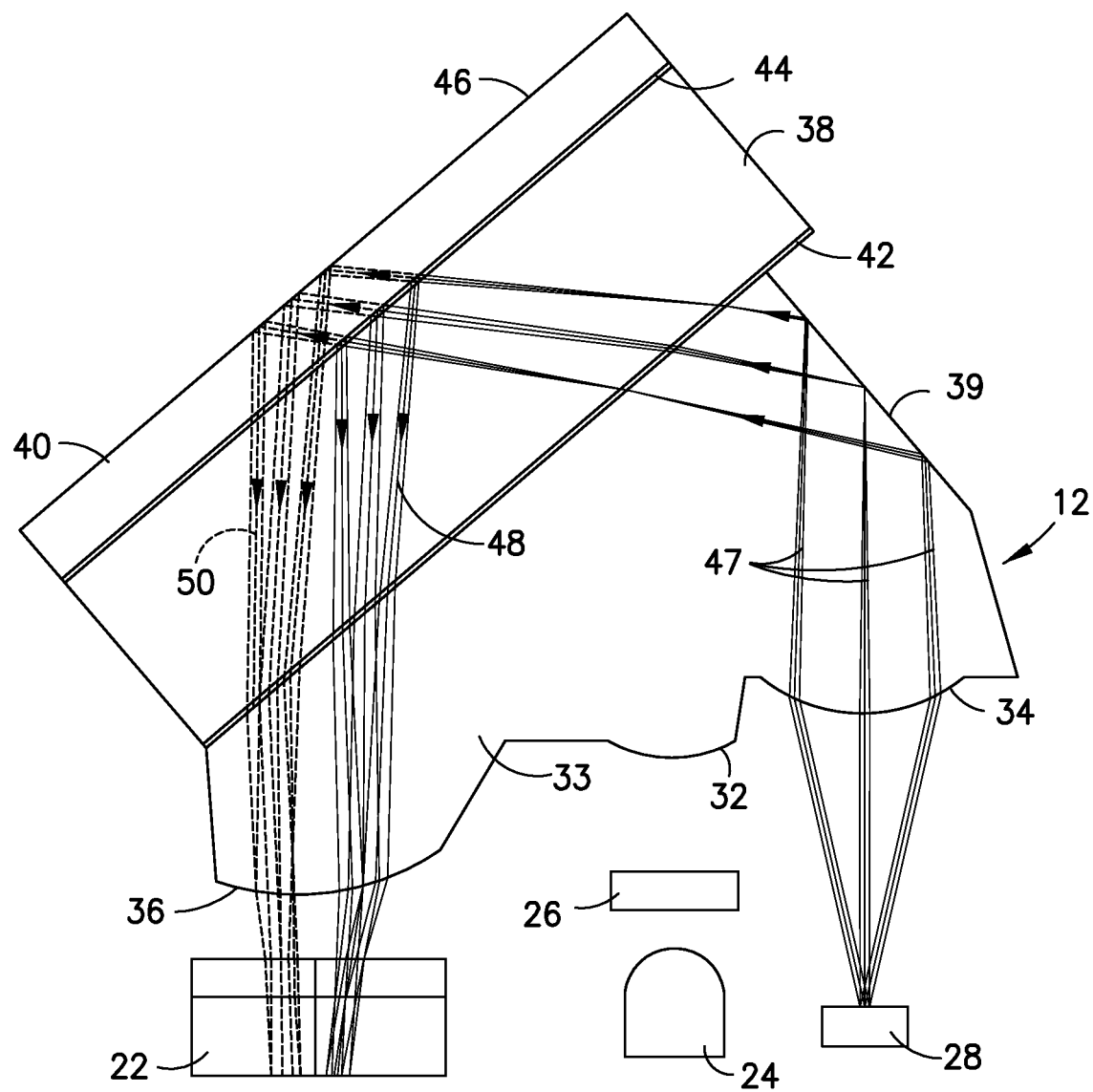
FIG. 3 is a schematic diagram of the CGM device of FIG. 1 including ray traces through the optical coupler, from the fiber face to a photodiode.

FIGS. 1-3 illustrate an illustrative embodiment of an on-body CGM sensor 10 utilizing optical interrogation using an optical coupler 12 in accordance with the present invention. The CGM sensor 10 includes a base 14 with a top surface 16 that supports the various components of the CGM sensor 10. A bottom surface 18 of the base 14 is used to support and adhere the CGM sensor on the skin of a user. A printed circuit board 20 is fixed to the top surface 16 of the base 14 and selectively controls power to a photodiode 22 and an LED 24, respectively fixed thereon. A cover 25 substantially encloses the components of the CGM sensor 10 and is fixed to the base 14.

The LED 24 emits light that is selectively filtered by a filter 26 fixed to a top surface of the LED 24. The optical coupler 12 is positioned above the LED 24 and photodiode 22 and directs the light emitted from the LED 24 into a fiber 28 positioned adjacent to the LED 24. The fiber 28 runs through the length of a needle 30. The needle 30 is used to insert the fiber 28 into a user to provide contact between the fiber 28 and biomaterial, such as GBP, beneath the skin of the user. The GBP coats or is deposited on the end of the needle 30 and contacts blood or interstitial fluid (ISF) after insertion into the user.

The optical coupler 12 includes a plastic connector 33 having three integral lenses, an LED lens 32, a fiber lens 34 and a detector lens 36. The plastic connector also includes a pair of inclined glass mounting surfaces 37 and a mirrored surface 39 that reflects light emitted from the LED 24 through the fiber lens 34 and into the fiber 28 to transmit light to the GBP. The glass mounting surfaces 37 are configured to support and fix filters at a predetermined angle with respect to the photodiode 22, the LED 24 and the fiber 28.

The optical coupler 12 includes a first glass filter 38 and a second glass filter 40. The first glass filter 38 is fixed to the second glass filter 40 via gluing or another desired securing mechanism. The glued first and second glass filters 38 and 40 are also fixed or glued to the inclined glass mounting surfaces 37.

The first glass filter 38 includes a first dichroic filter coating 42 on the surface of the glass filter 38 mounted to the glass mounting surfaces 37. The first dichroic filter coating 42 reflects the light wavelengths emitted by the LED and transmits emission light wavelengths emitted from the GBP via the fiber 28.

The second glass filter 40 includes a second dichroic filter coating 44 on the same surface that is mounted to the first glass filter 38. The second dichroic filter coating 44 reflects shorter emission wavelengths representing a signal band and transmits longer wavelengths representing a reference band. A mirror surface 46 is formed on the surface of the second glass filter 40 opposite to the surface mounted to the first glass filter 38. The mirrored surface 46 reflects all wavelengths, but is particularly used to reflect the long wavelengths transmitted by the second dichroic filter coating 44.

FIG. 2 illustrates a schematic diagram of the CGM sensor 10 in accordance with an illustrative embodiment of the present invention, including ray traces representing the light path from the LED 24 through the optical coupler 12 to the fiber 28 for illuminating the GBP in contact with an end of the fiber 28. Light 45 is first emitted from the LED 24 and filtered by the filter 26. The light 45 then travels through the LED lens 32 which focuses and directs the light 45 toward the first dichroic coating 42 which reflects the light 45 toward the mirrored surface 39 of the optical coupler 12. The mirrored surface 39 then reflects the light 45 toward the fiber lens 34 which focuses and transmits the light 45 toward the fiber 28 which illuminates the GBP (not shown).

FIG. 3 illustrates a schematic diagram of the CGM sensor 10 in accordance with an illustrative embodiment of the present invention, including ray traces representing the light path from the fiber 28 through the optical coupler 12 to the photodiode 22 for capturing the reference band and the signal band wavelengths. Light 47 is emitted from the GBP through the fiber 28 and transmitted toward the fiber lens 34. The light 47 then travels through the fiber lens 34 which focuses the light 47 and directs it toward the mirrored surface 39 which reflects the light 47 toward the first dichroic coating 42 which transmits the light 47 toward the second dichroic coating 44.

The first dichroic coating 42 can be configured to filter the light 47 emitted by the GBP by reflecting only desired wavelengths and transmitting only the wavelengths that make up the signal and reference band wavelengths 48 and 50. The second dichroic coating 44 can be configured to further filter the light 47 by reflecting only the wavelengths of the signal band and transmitting all other wavelengths.

The signal band wavelength 48 reflects off the second dichroic coating 44 and passes at an angle through the first glass filter 38 and optical coupler 12. The signal band wavelength 48 is then focused by the detector lens 36 onto the photodiode 22.

After the signal band wavelength 48 is reflected off the second dichroic coating 44, only the reference band wavelength 50 remains, due to the filtering that occurs at the first dichroic coating 42. The reference band wavelength 50 is transmitted toward the mirrored surface 46 on the back surface of the second glass filter 40 which reflects all remaining wavelengths due to total internal reflection, or by having a silvered surface, which would also provide total reflection of remaining wavelengths.

The light of the reference band continues back through the second glass filter 40 and passes through the first glass filter 38 and re-enters the optical coupler 12 and is focused by the detector lens 36 onto the photodiode 22.

The above defined fiber optic CGM device 10 can be housed within a cover 25, as described previously, or modified to utilize the illustrative OBS covers described below. Additionally, alternative optical CGM devices known in the art can also be modified to include the illustrative OBS covers described below.

An OBS cover encloses and protects the CGM device 10 from environmental conditions that may adversely affect and/or damage the components of the CGM device 10.

Figure 4:
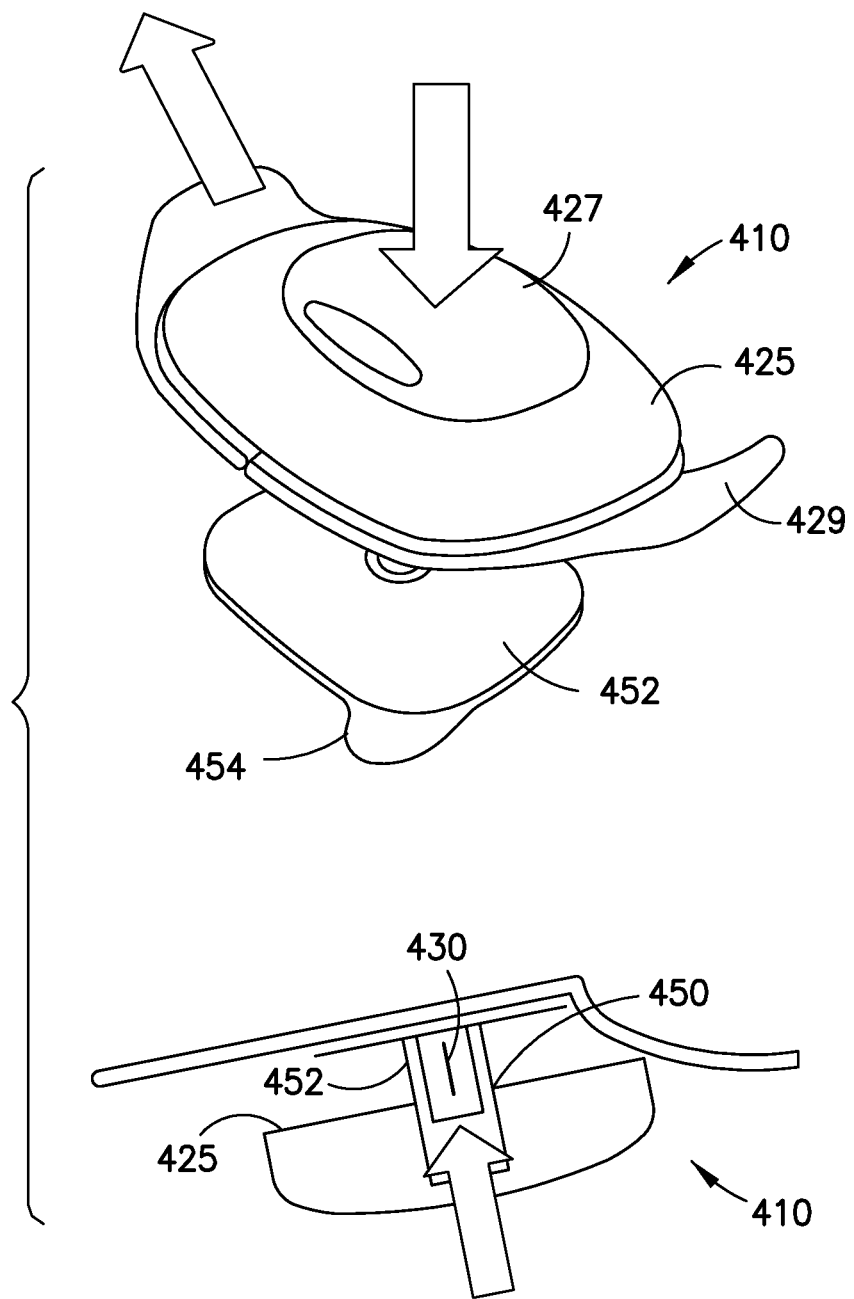
FIG. 4 shows an illustrative embodiment of an OBS device in accordance with the present invention.

FIG. 4 shows an illustrative embodiment of an OBS 410 having a cover 425 for enclosing and protecting a CGM device (not shown) in accordance with the present invention. The cover 425 includes a handle 427 and an adhesive release paper 429 that can be removed to expose an adhesive layer or coating on a bottom surface of the cover 425. The adhesive coating can be used to secure the OBS 410 to the skin of a user during use. The cover 425 also includes a recessed portion 450 that receives a needle inserter assembly 452. The needle inserter assembly 452 aids in stabilizing the cover 425 and needle 430 during injection into the user. The needle inserter assembly 452 also includes a removable film 454 that exposes an adhesive layer or coating on a bottom surface of the needle inserter assembly 452, thereby securing the needle inserter assembly 452 to the skin of the user during injection of the needle 430 and during use of the OBS 410. The needle 430 is injected into the user by applying a force to the handle 427 in the direction of the user, which forces the cover 425 to receive the needle inserter assembly 452 while forcing the needle 430 into the user.

FIG. 5 shows an illustrative embodiment of an OBS 510 having a cover 525 and an adhesive release paper 529 in accordance with the present invention. The adhesive release paper 529 includes opposing flaps that can be joined together above the cover 525, opposite the user interface side. The opposing flaps of the release paper 529 form a handle 527 when joined together, via an adhesive or by constant pressure by the user. The handle 527 can be used to position the OBS 510 on the skin of the user and can be removed once the OBS 510 is secured to the skin of the user.

FIG. 6 shows an illustrative embodiment of an OBS of an OBS 610, having a cover 625 with an integrated needle inserter 652. The needle inserter 652 can be pressed to insert a needle into the user. The needle inserter 652 can be colored to match the cover 625, thereby reducing the attention drawn to the needle inserter 652. The needle inserter can also be colored to contrast the cover 625.

FIG. 7 shows an illustrative embodiment of an OBS of an OBS 710, having a cover 725 and an integrated handle 727 for positioning and applying the OBS 710 to the user. The cover 725 and the handle 727 each have an hourglass-like shape. The cover 725 can be formed from a semi-flexible material to provide sufficient support for the OBS 710 and comfort to the user.

FIG. 8 shows an illustrative embodiment of an OBS 810, having a cover 825 and an integrated handle 827 for positioning and applying the OBS 810 to the user. The cover 825 and the handle 827, each having an hourglass-like shape. The cover 825 can be formed from a material having a soft leather feel to provide additional comfort to the user during use.

Figure 9:
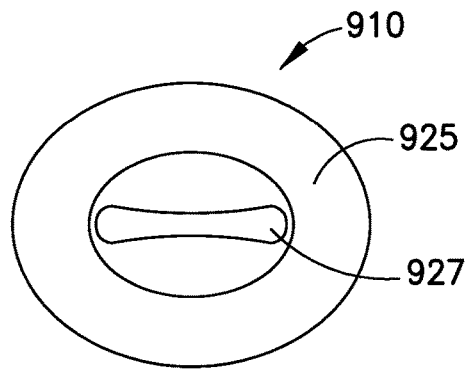
FIG. 9 shows another illustrative embodiment of an OBS device in accordance with the present invention, having a handle with a substantially narrow and elongated shape with indentations.

FIG. 9 shows an illustrative embodiment of an OBS 910, having a cover 925 and an integrated handle 927 for positioning and applying the OBS 910 to the user. The handle 927 having a substantially narrow and elongated shape. The cover 925 can be formed by silicone to provide addition comfort to the user while maintain sufficient support for the OBS 910.

Figure 10A:
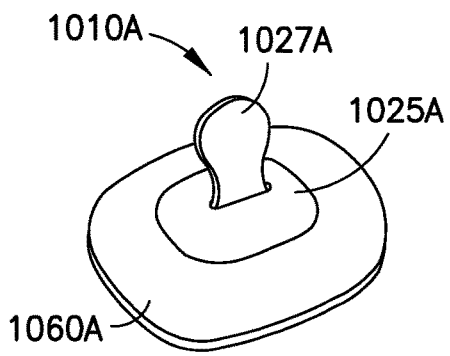
FIG. 10A shows another illustrative embodiment of an OBS device in accordance with the present invention, having a flange and a handle for removal which folds flat.

FIG. 10A shows an illustrative embodiment of an OBS 1010A, having a cover 1025A, a flange 1060A and a handle 1027A. The shape and profile of the cover 1025A provide structural support and comfort to the user during use. The handle 1027A can be used to position and apply the OBS 1010A on the user. The handle 1027A can be made of a fabric material or another desired flexible and durable material.

Figure 10B:
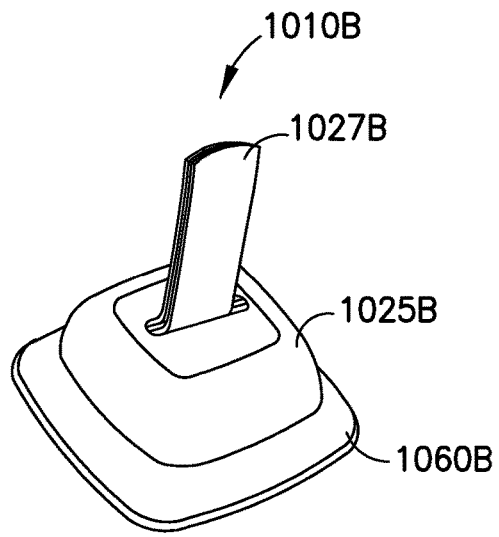
FIG. 10B shows another illustrative embodiment of an OBS device in accordance with the present invention, having a flange and a handle for removal which folds flat.
Figure 10C:
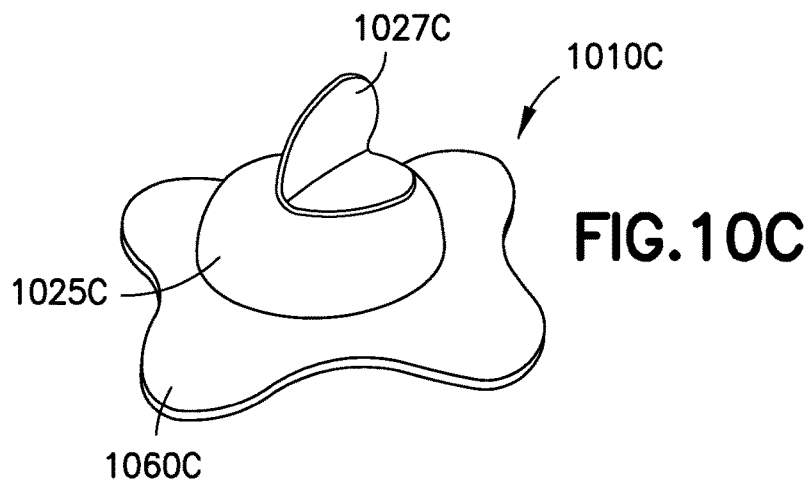
FIG. 10O shows another illustrative embodiment of an OBS device in accordance with the present invention, having a flange and a handle for removal which folds flat.

FIG. 10B shows an illustrative embodiment of an OBS 1010B, having a cover 1025B, a flange 1060B and a handle 1027B. The shape and profile of the cover 1025B provides structural support and comfort to the user during use. The handle 1027B can be used to position and apply the OBS 1010B on the user. The handle 1027B can be made of a fabric material or another desired flexible and durable material.

FIG. 10O shows an illustrative embodiment of an OBS 1010C, having a cover 1025C, a flange 1060C and a handle 1027C. The shape and profile of the cover 1025C provides structural support and comfort to the user during use. The handle 1027C can be used to position and apply the OBS 1010C on the user. The handle 1027C can be made of a fabric material or another desired flexible and durable material.

Figure 11:
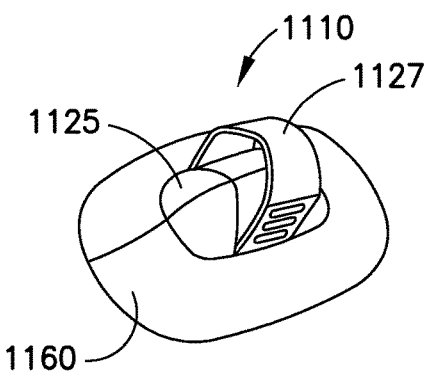
FIG. 11 shows another illustrative embodiment of an OBS device in accordance with the present invention, having a handle that can be recessed within a cover.

FIG. 11 shows an illustrative embodiment of an OBS 1110 having a cover 1125, a flange 1160 and a handle 1127. The handle 1127 can extend from the cover 1125 during positioning and application of the OBS 1110 on the user and can be recessed within the cover 1125 during use of the OBS 1110 to reduce the overall profile of the OBS 1110.

Figure 12:
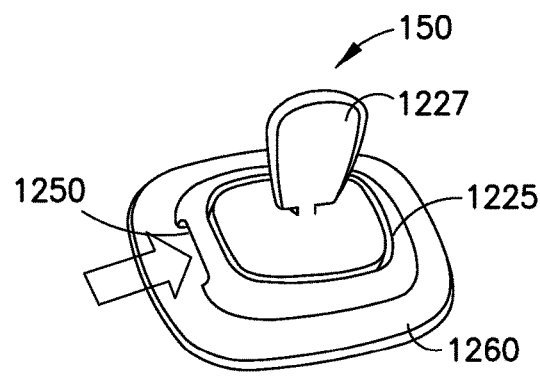
FIG. 12 shows another illustrative embodiment of an OBS device in accordance with the present invention, having a frangible or foldable handle.

FIG. 12 shows an illustrative embodiment of an OBS 1210 having a cover 1225, a flange 1260 and a handle 1227. The handle 1227 can aid in positioning the OBS 1210 on the user. After the OBS 1210 is positioned on the user the handle 1227 can be broken off and separated from the cover 1225 and stowed in a recess 1250 between the cover 1225 and the flange 1260. Breaking off the handle 1227 reduces the profile of the OBS 1210, reducing the possibility for accidental snagging of the OBS 1210 during use.

Figure 13A:
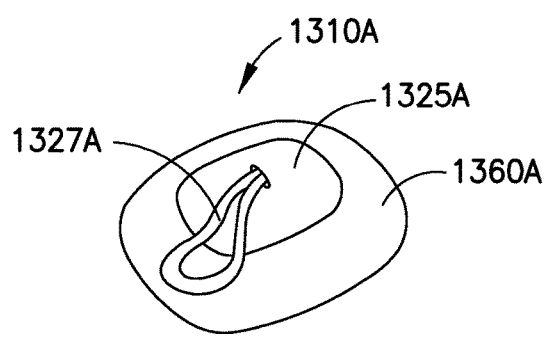
FIG. 13A shows another illustrative embodiment of an OBS device in accordance with the present invention, having a lanyard-style handle.

FIG. 13A shows an illustrative embodiment of an OBS 1310A, having a cover 1325A, a flange 1360A and a lanyard-style handle 1327A. The lanyard handle 1327A enables the user to more easily position the OBS 1310A on the user without significantly increasing the profile of the OBS 1310A.

Figure 13B:
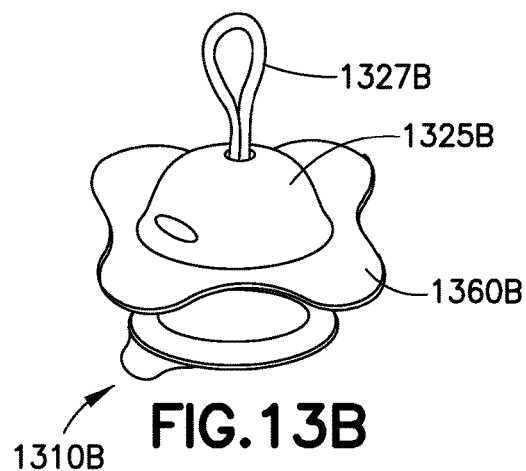
FIG. 13B shows another illustrative embodiment of an OBS device in accordance with the present invention, having a lanyard-style handle.

FIG. 13B shows an illustrative embodiment of an OBS 1310B, having a cover 1325B, a flange 1360A and a lanyard-style handle 1327B. The lanyard handle 1327B enables the user to more easily position the OBS 1310B on the user without significantly increasing the profile of the OBS 1310B.

Figure 14:
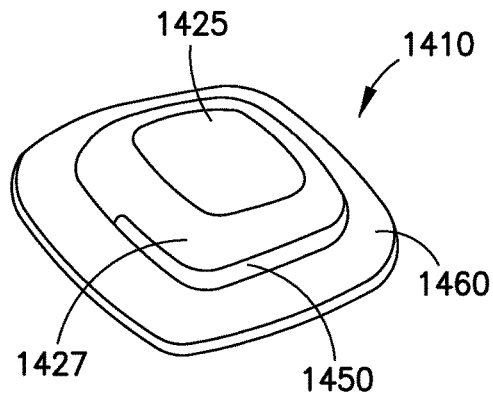
FIG. 14 shows another illustrative embodiment of an OBS device in accordance with the present invention, having a recess providing a hinged handle portion.

FIG. 14 shows an illustrative embodiment of an OBS 1410 having a cover 1425 and a flange 1460. A recess 1450 is formed between the cover 1425 and the flange 1460 which provides a handle portion 1427 that enables the user to more easily grab and position the OBS 1410 without significantly increasing the profile of the OBS 1410. The handle portion 1427 can also be rotatable with respect to the flange 1460.

Figure 15:
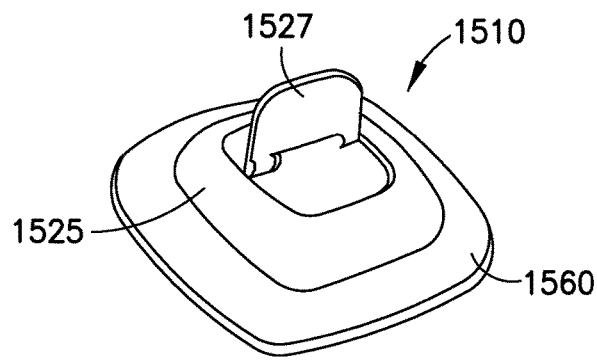
FIG. 15 shows another illustrative embodiment of an OBS device in accordance with the present invention, having a hinged handle.

FIG. 15 shows an illustrative embodiment of an OBS 1510 having a cover 1525 and a flange 1560. A handle 1527 is hinged to a top surface of the cover 1525 such that the handle 1527 is substantially perpendicular to the top surface of the cover 1525 when utilized and handled by the user. When the user is done using the handle 1527, the handle 1527 can be rotated to a substantially parallel position with respect to the top surface of the cover 1525, reducing the profile of the OBS 1510.

Figure 16:
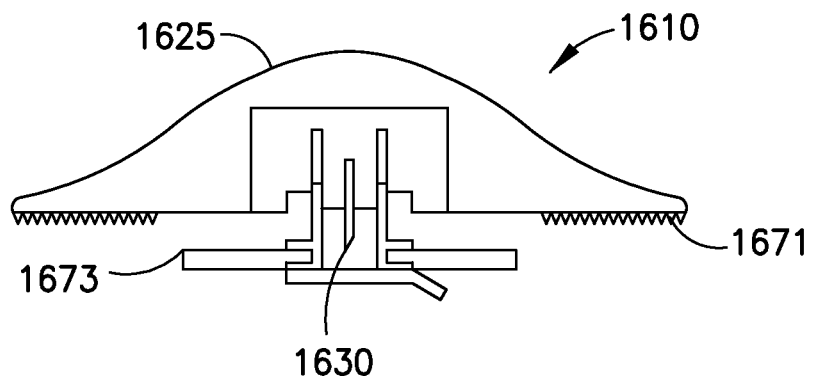
FIG. 16 shows another illustrative embodiment of an OBS device in accordance with the present invention, having a telescoping stabilizer.

FIG. 16 shows an illustrative embodiment of an OBS 1610 having a cover 1625 and an adhesive layer 1671 on an underside thereof. OBS 1610 also includes a telescoping stabilizer 1673 that can be secured to a user and acts as a guide during needle 1630 insertion. The telescoping stabilizer 1673 is received into the body of the cover 1625 during insertion of the needle 1630 forming a low profile OBS having an integrated telescoping stabilizer 1673.

Figure 17A:
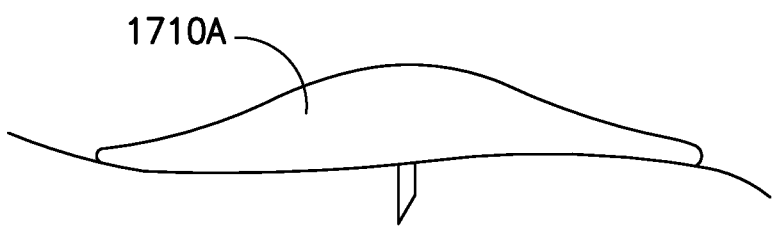
FIG. 17A shows another illustrative embodiment of an OBS device in accordance with the present invention, having a gradual reduced thickness.

FIG. 17A shows an illustrative embodiment of an OBS 1710A. OBS 1710A has a gradual reduced thickness from a central position out to a peripheral position which reduces flex and micro-motion.

Figure 17B:
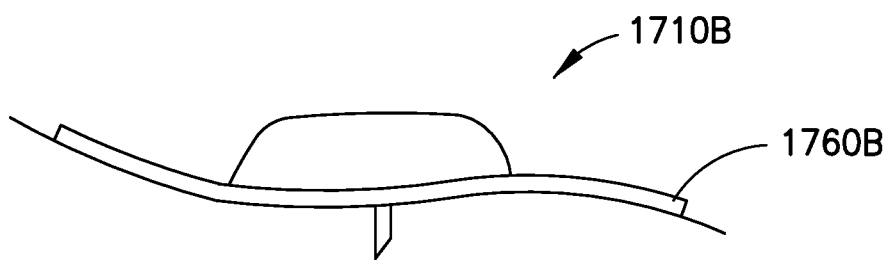
FIG. 17B shows another illustrative embodiment of an OBS device in accordance with the present invention, having a gradual reduced thickness.

FIG. 17B shows an illustrative embodiment of an OBS 1710B. OBS 1710B has a more abrupt reduction in thickness, but includes a thin flange 1760B which enables more flex and micro-motion.

Figure 18:
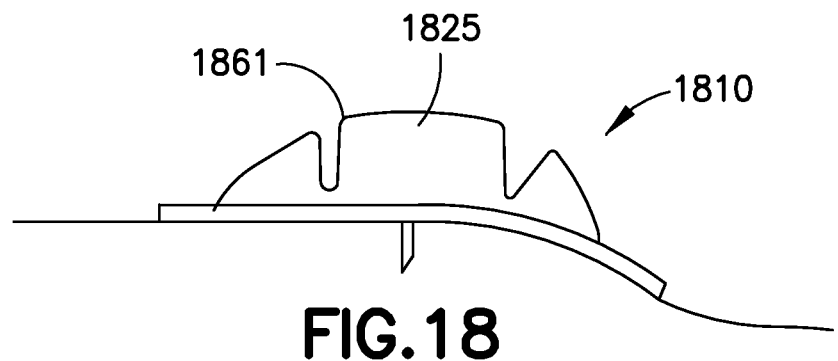
FIG. 18 shows another illustrative embodiment of an OBS device in accordance with the present invention, having a cover with cutout portions.

FIG. 18 shows an illustrative embodiment of an OBS 1810 including a cover 1825 having cutout portions 1861 that enable independent flexibility of the perimeter of the cover 1825 while maintaining a sensor in a substantially fixed position.

Figure 19:
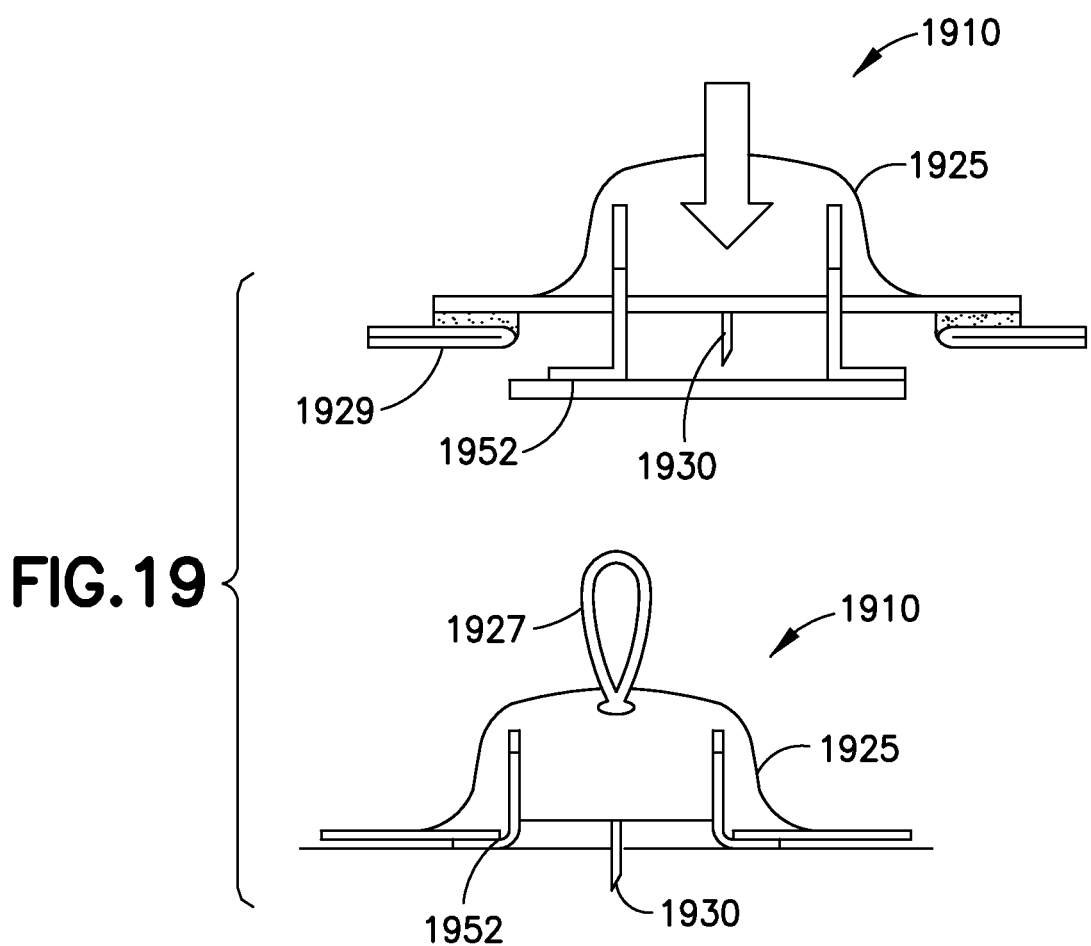
FIG. 19 shows another illustrative embodiment of an OBS device in accordance with the present invention, having a cover with peelable corners.

FIG. 19 shows an illustrative embodiment of an OBS 1910 including a cover 1925 and a needle inserter 1952. The needle inserter 1952 protects the needle 1930 and provides stability during needle insertion. A fabric handle 1927 is fixed to the cover 1925 and flexes to a substantially flat profile during use of the OBS 1910. To apply the OBS 1910 a user removes release paper 1929 from adhesive on the underside of the cover 1925 and presses the cover 1925 against the skin of the user. The needle inserter 1952 is received within the body of the cover 1925 as the needle insertion takes place. To remove the OBS 1910 from the user, the user peels the corners of the cover 1925 and pulls up on the handle 1927.

Figure 20:
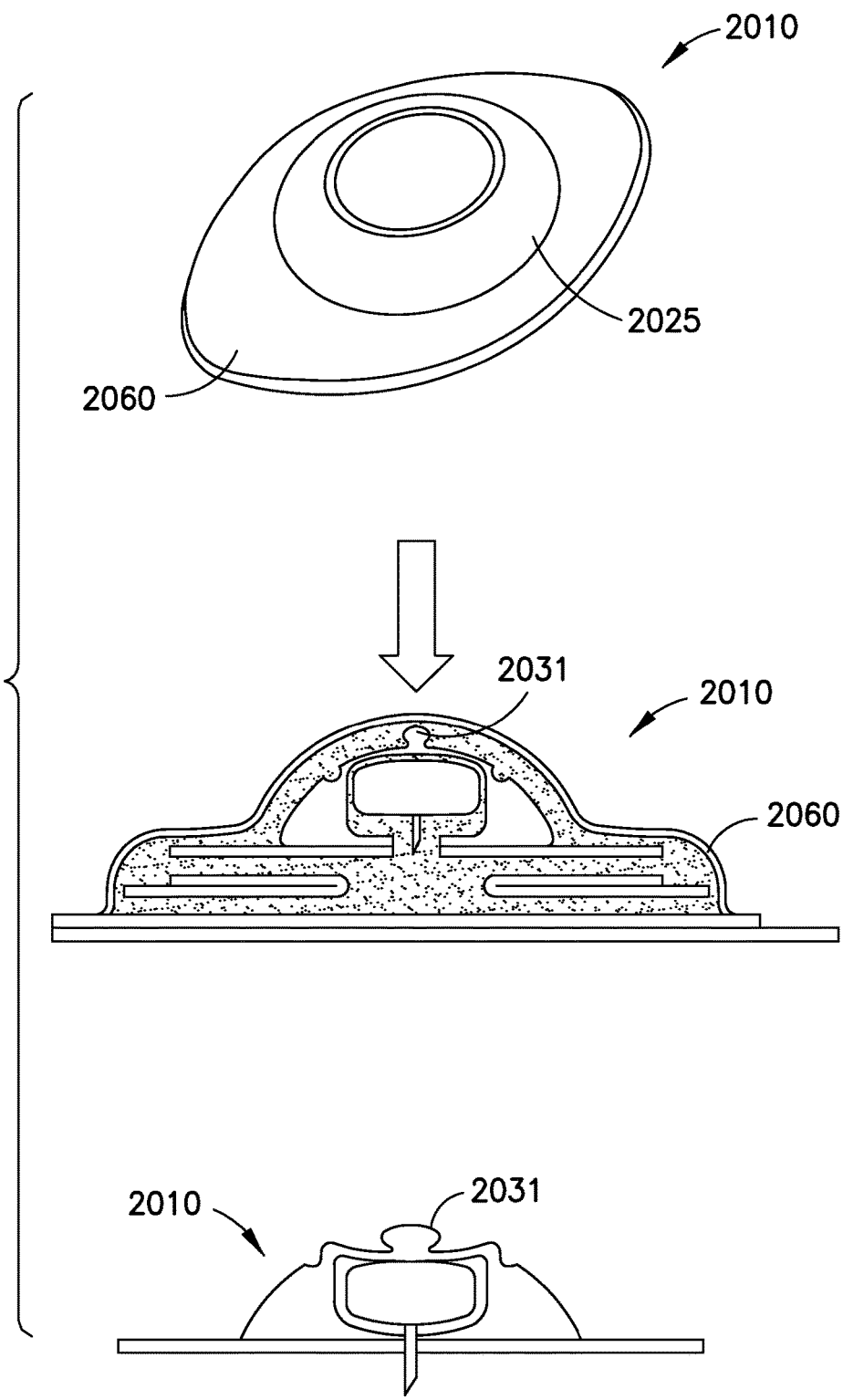
FIG. 20 shows another illustrative embodiment of an OBS device in accordance with the present invention, having a knob that aids in inserting and removing a needle.

FIG. 20 shows an illustrative embodiment of an OBS 2010 having a cover 2025 and a flange 2060. The OBS 2010 also includes a knob 2031 that aids in inserting and removing a needle. The user pushes against the knob 2031 to insert the needle and pulls upward on the handle to remove the needle from the user.

Figure 21A:
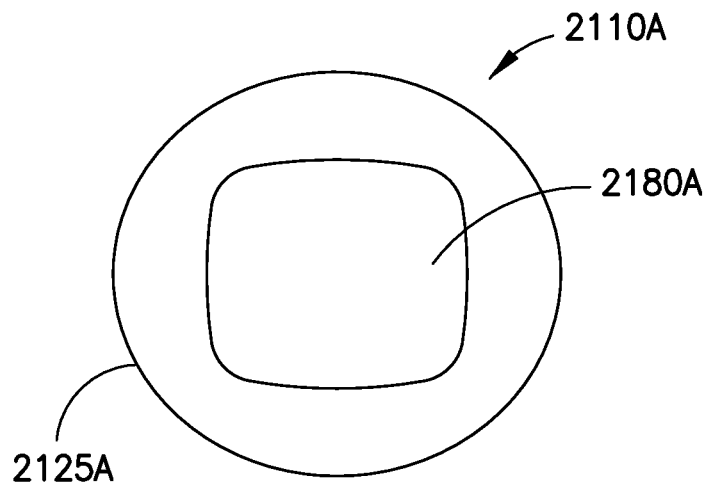
FIG. 21A shows another illustrative embodiment of an OBS device in accordance with the present invention, having a window and a flexible cover.

FIG. 21A shows an illustrative embodiment of an OBS 2110A. OBS 2110A includes a window 2180A and a flexible cover 2125A. The window 2180A enables a user to visually inspect a CGM device within the cover 2125A.

Figure 21B:
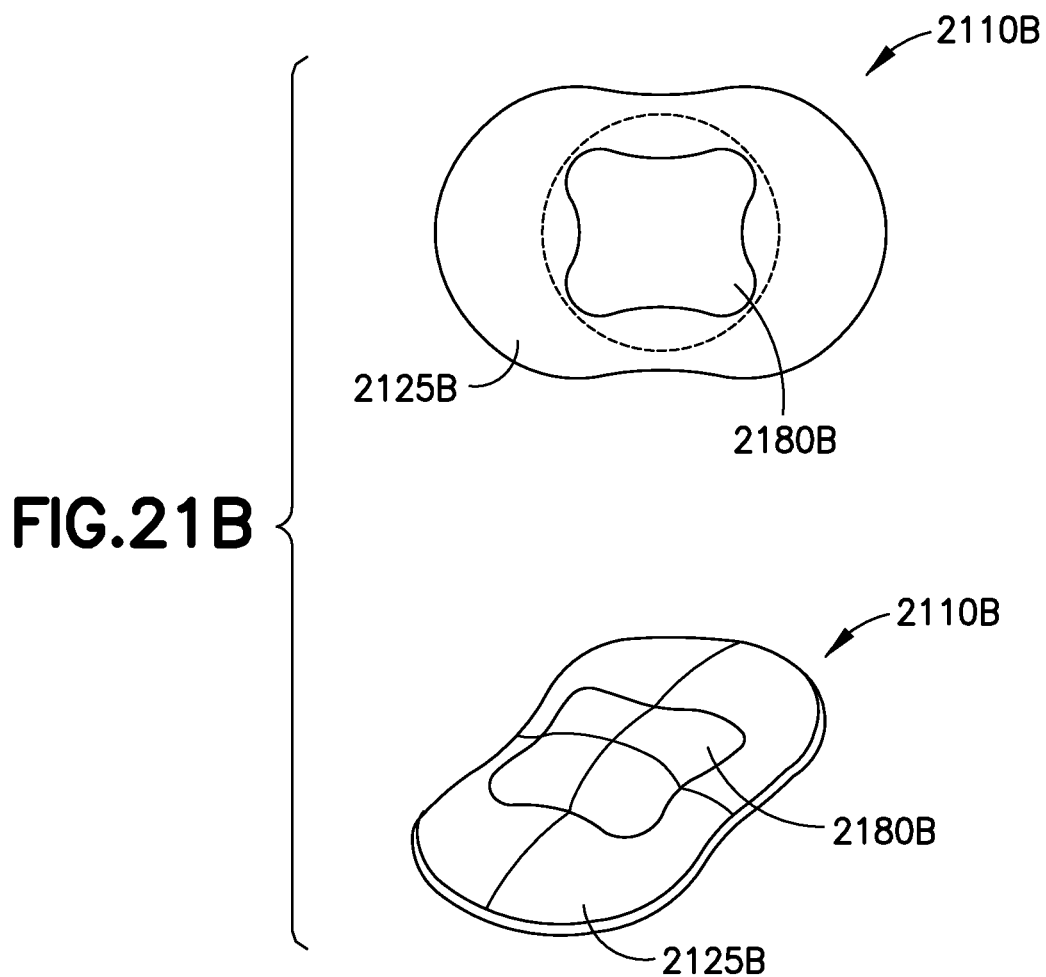
FIG. 21B shows another illustrative embodiment of an OBS device in accordance with the present invention, having a window and a flexible cover.

FIG. 21B shows an illustrative embodiment of an OBS 2110B. OBS 2110B includes a window 2180B and a flexible cover 2125B. The window 2180B enables a user to visually inspect a CGM device within the cover 2125B.

Figure 22:
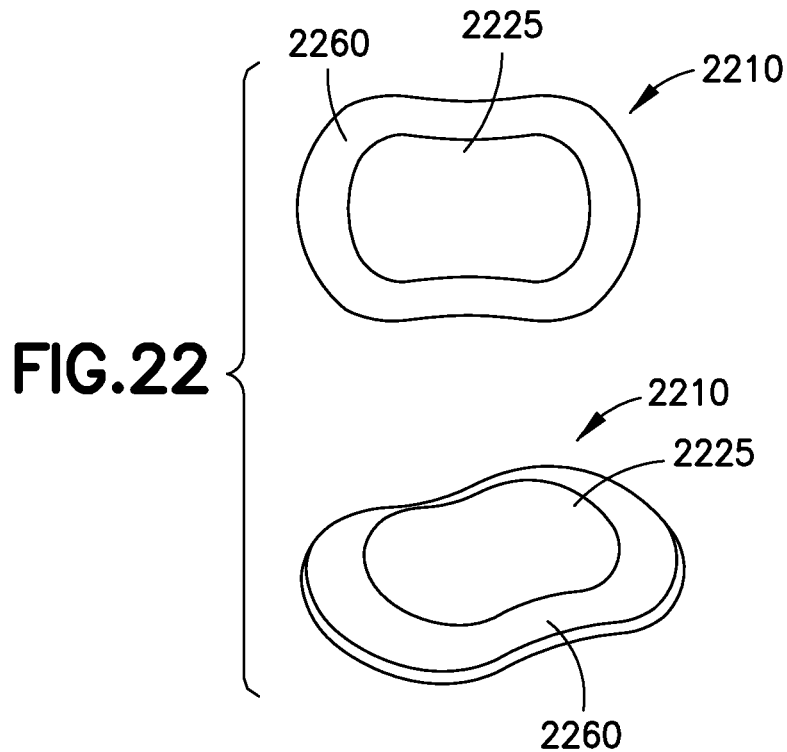
FIG. 22 shows another illustrative embodiment of an OBS device in accordance with the present invention, having an hourglass-shaped cover and flange.

FIG. 22 shows an illustrative embodiment of an OBS 2210 having an hourglass-shaped cover 2225 and flange 2260.

Figure 23:
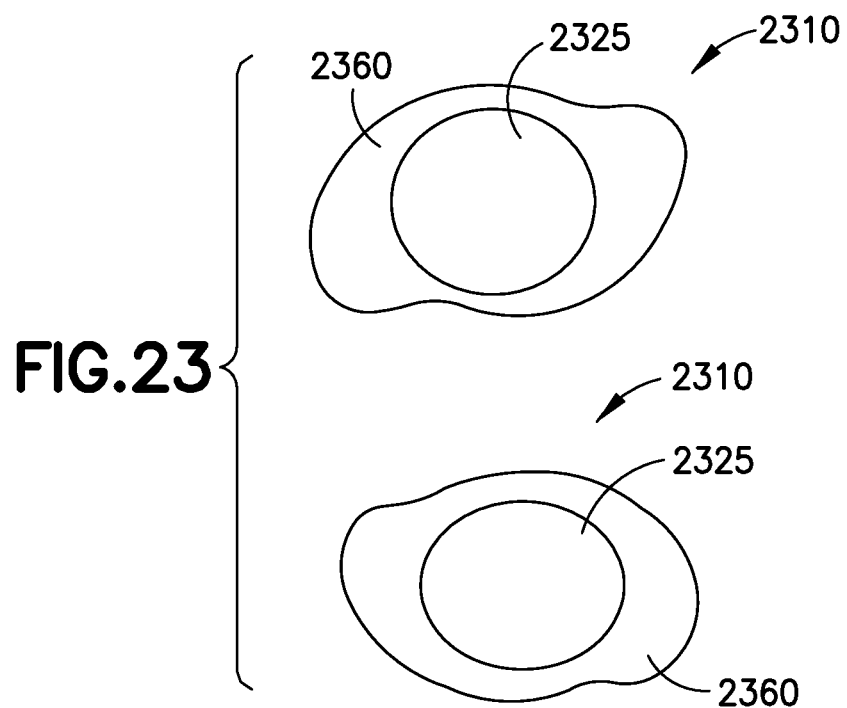
FIG. 23 shows another illustrative embodiment of an OBS device in accordance with the present invention, having a cover and a non-symmetrical-shaped flange.

FIG. 23 shows an illustrative embodiment of an OBS 2310 having a cover 2325 and a non-symmetrical-shaped flange 2360.

FIG. 24 shows an illustrative embodiment of an OBS 2410 having a cover 2425 and a compound curved-shaped flange 2460.

FIG. 25 shows an illustrative embodiment of an OBS 2510 having a cover 2525, a separate battery pod 2581 to house a battery for a CGM device, and a flange 2560.

Figure 26:
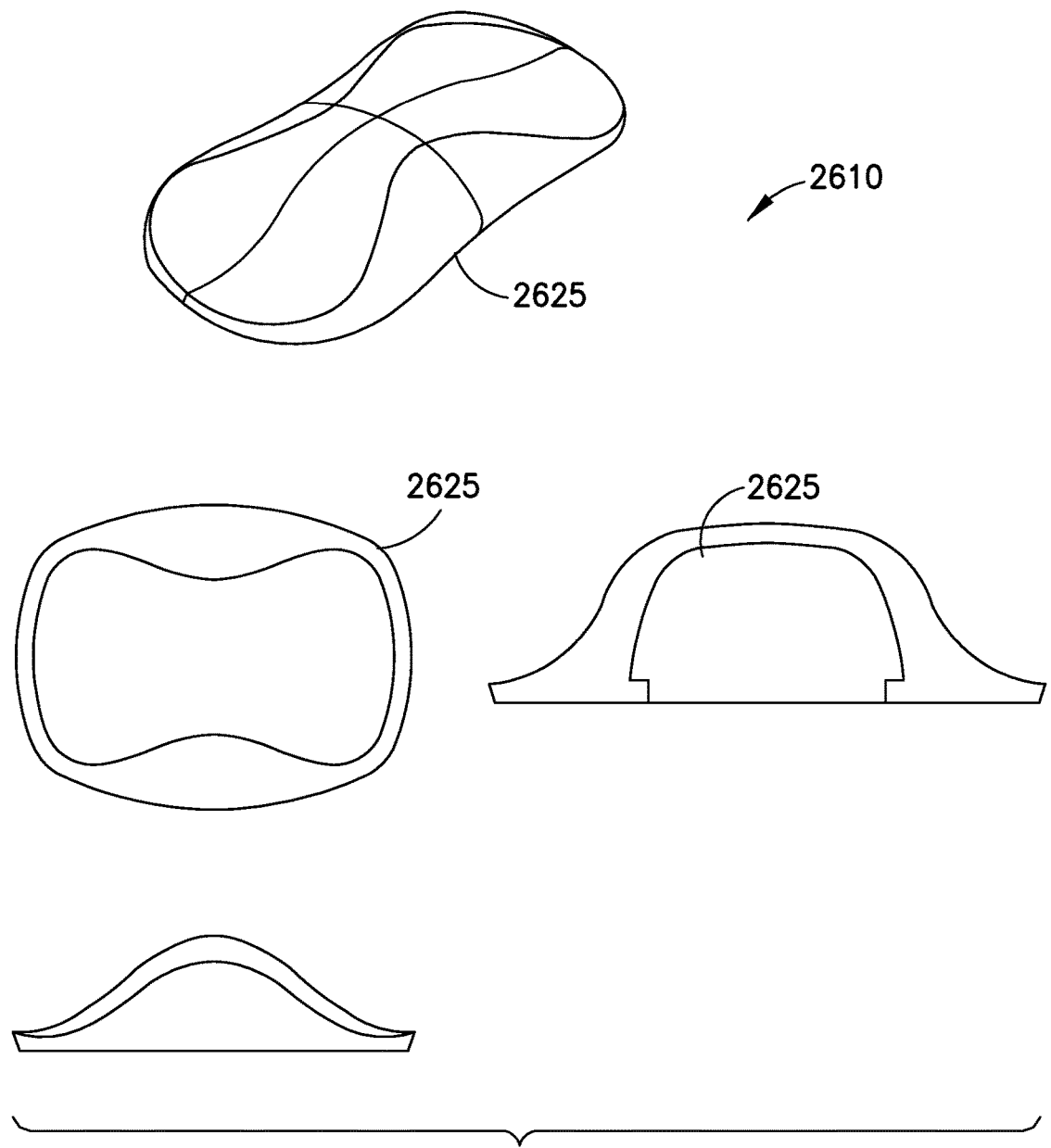
FIG. 26 shows another illustrative embodiment of an OBS device in accordance with the present invention, having a sloped flexible cover.

FIG. 26 shows an illustrative embodiment of an OBS 2610 having a sloped flexible cover 2625.

Figure 27:
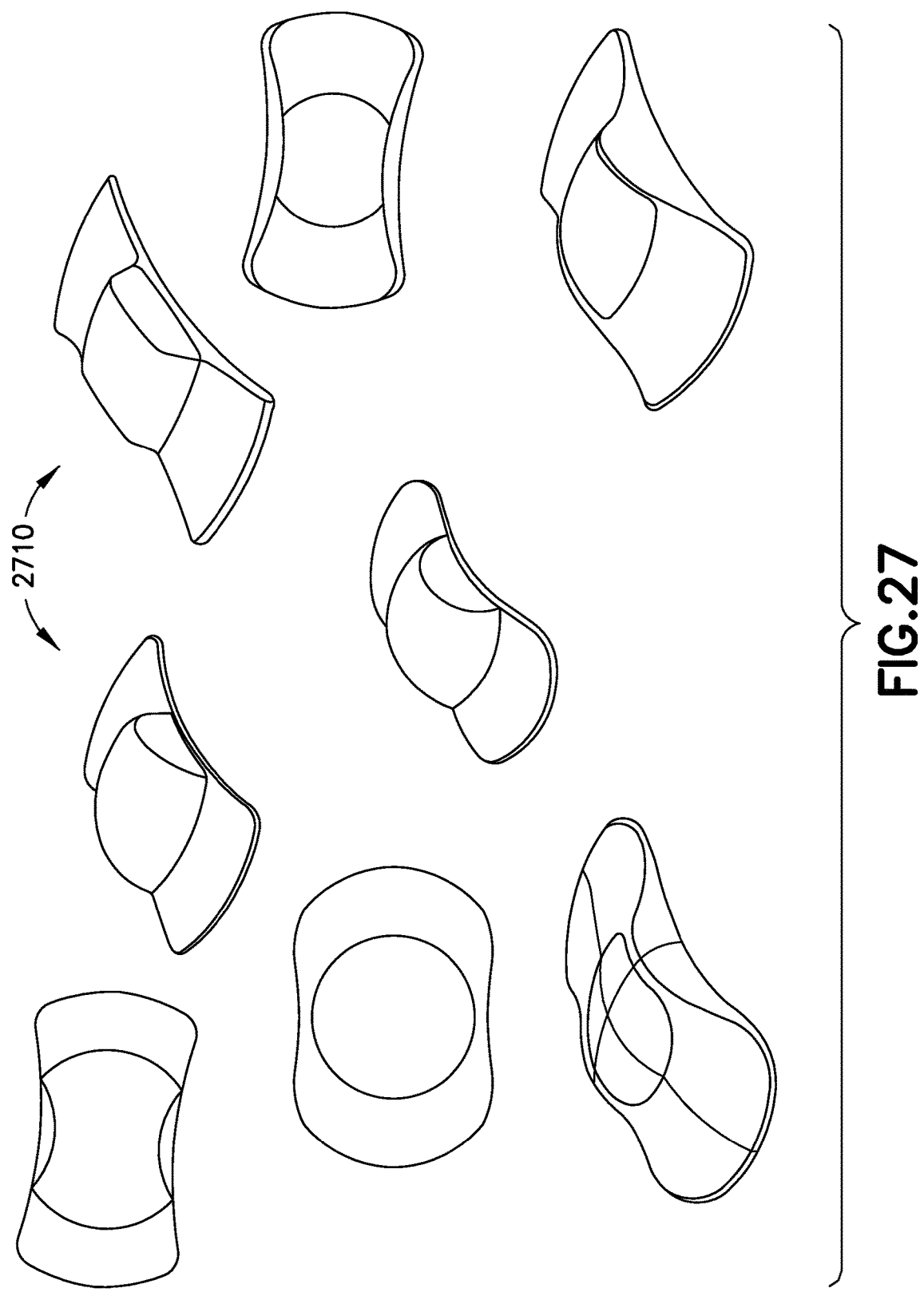
FIG. 27 shows other illustrative embodiments of an OBS device in accordance with the present invention, having scooped sides.

FIG. 27 shows illustrative embodiments of an OBS 2710 having scooped sides.

Figure 28:
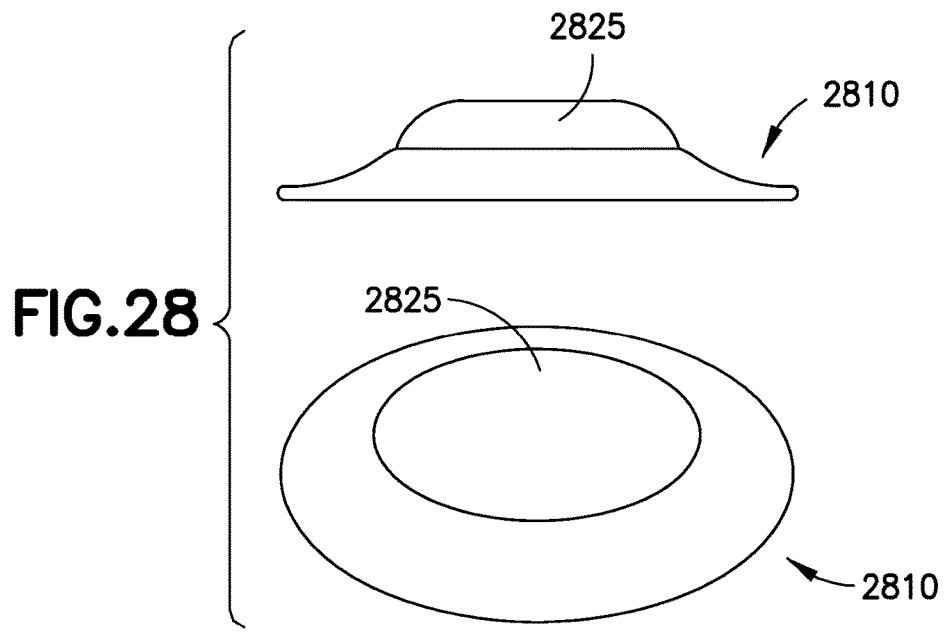
FIG. 28 shows another illustrative embodiment of an OBS device in accordance with the present invention, having a cover formed of a foam-like material.

FIG. 28 shows an illustrative embodiment of an OBS 2810 having a cover 2825 formed of a foam-like material providing a partial bumper for the OBS 2810.

Figure 29:
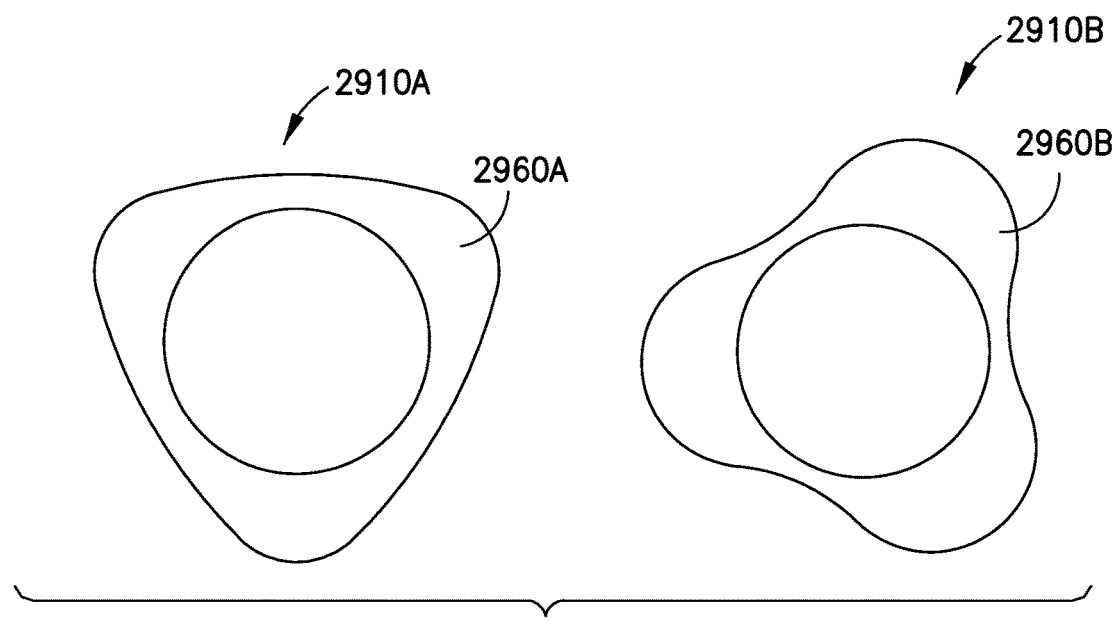
FIG. 29 shows another illustrative embodiment of an OBS device in accordance with the present invention, having substantially triangular flanges.

FIG. 29 shows illustrative embodiments of OBS devices 2910A and 2910B having corresponding substantially triangular flanges 2960A and 2960B.

Figure 30:
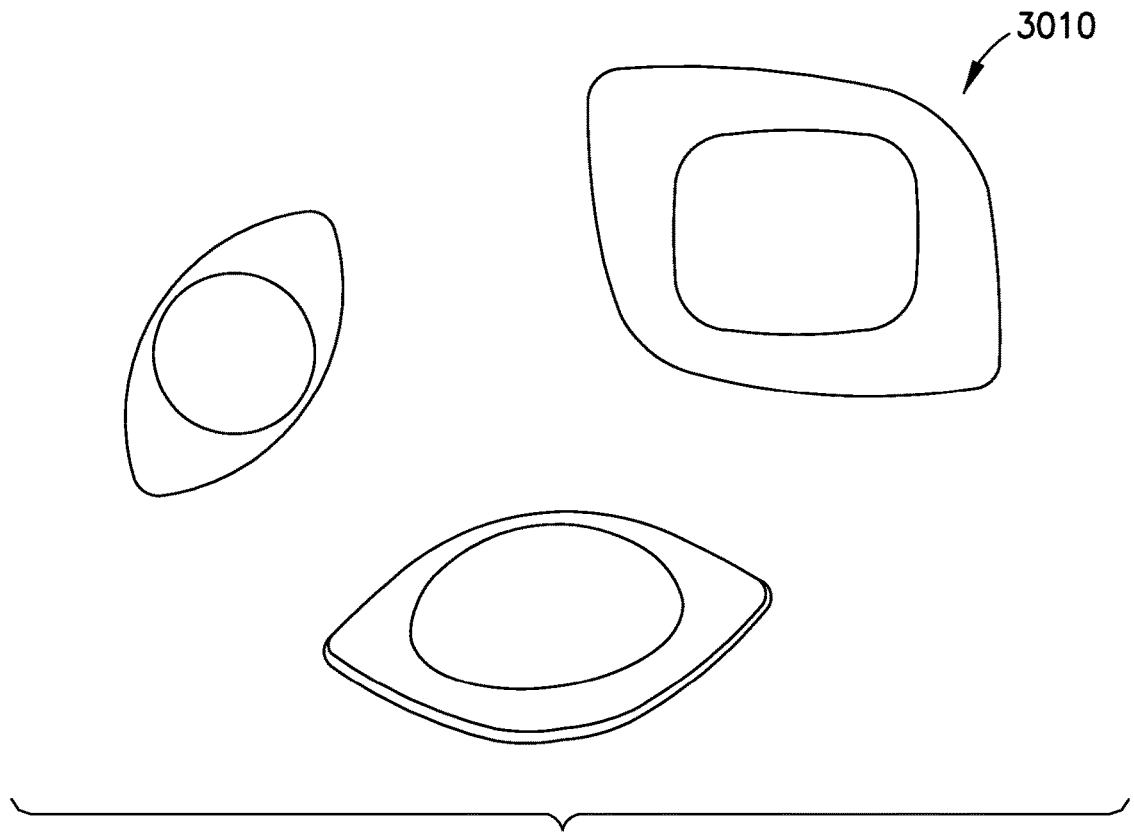
FIG. 30 shows another illustrative embodiment of an OBS device in accordance with the present invention, being substantially diamond-shaped.

FIG. 30 shows an illustrative embodiment of an OBS 3010 being substantially diamond-shaped.

Figure 31:
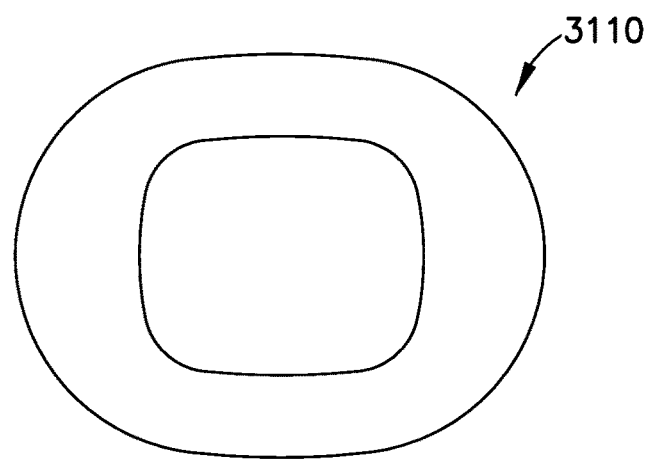
FIG. 31 shows another illustrative embodiment of an OBS device in accordance with the present invention, having subtle curved outer edges.

FIG. 31 shows an illustrative embodiment of an OBS 3110 having subtle curved outer edges.

Figure 32:
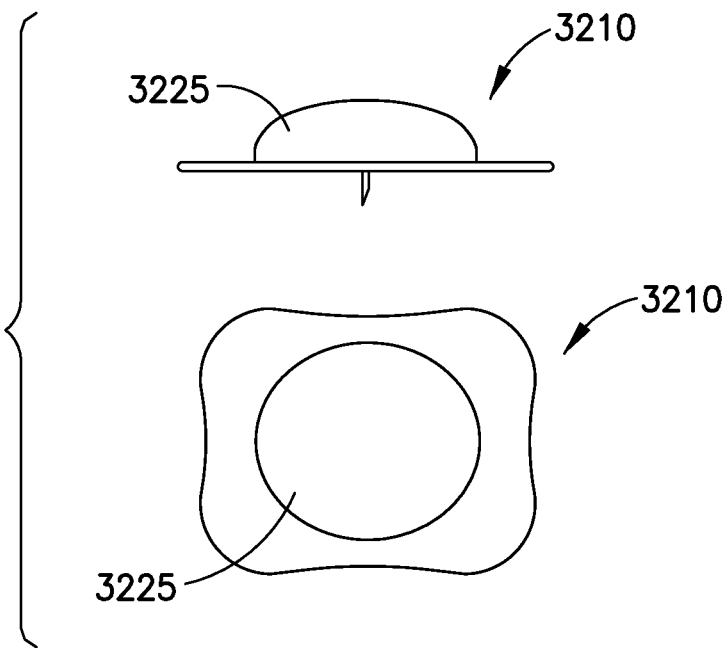
FIG. 32 shows another illustrative embodiment of an OBS device in accordance with the present invention, having a cover with no bumper portion and a low profile.

FIG. 32 shows an illustrative embodiment of an OBS 3210 having a cover 3225 with no bumper portion and a low profile. For example, the profile of the cover 3225 may be substantially 8 mm.

Figure 33:
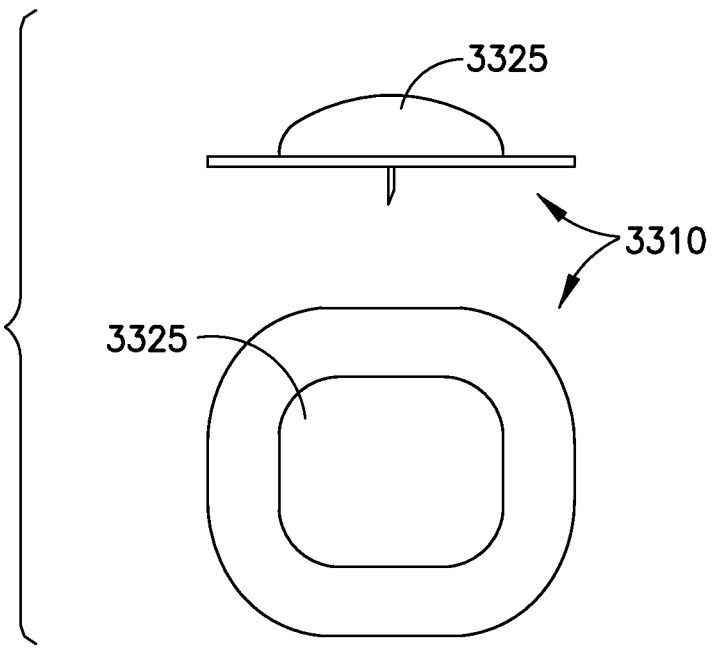
FIG. 33 shows another illustrative embodiment of an OBS device in accordance with the present invention, having a cover with no bumper portion and a low profile.

FIG. 33 shows an illustrative embodiment of an OBS 3310 having a cover 3325 with no bumper portion and a low profile. For example, the profile of the cover 3325 may be substantially 8 mm.

Figure 34:
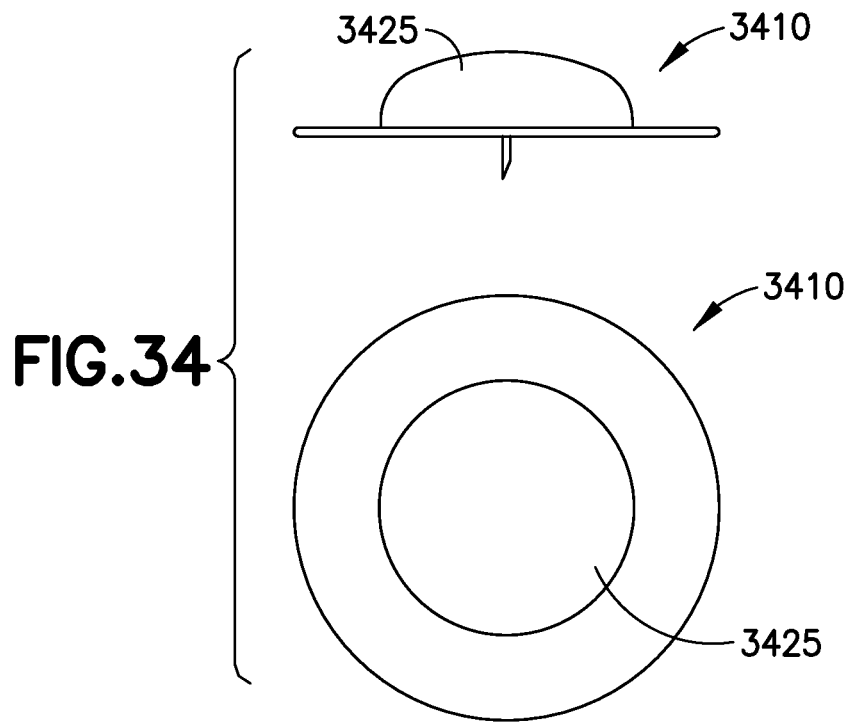
FIG. 34 shows another illustrative embodiment of an OBS device in accordance with the present invention, having a cover with no bumper portion and a low profile.

FIG. 34 shows an illustrative embodiment of an OBS 3410 having a cover 3425 with no bumper portion and a low profile. For example, the profile of the cover 3425 may be substantially 8 mm.

Figure 35:
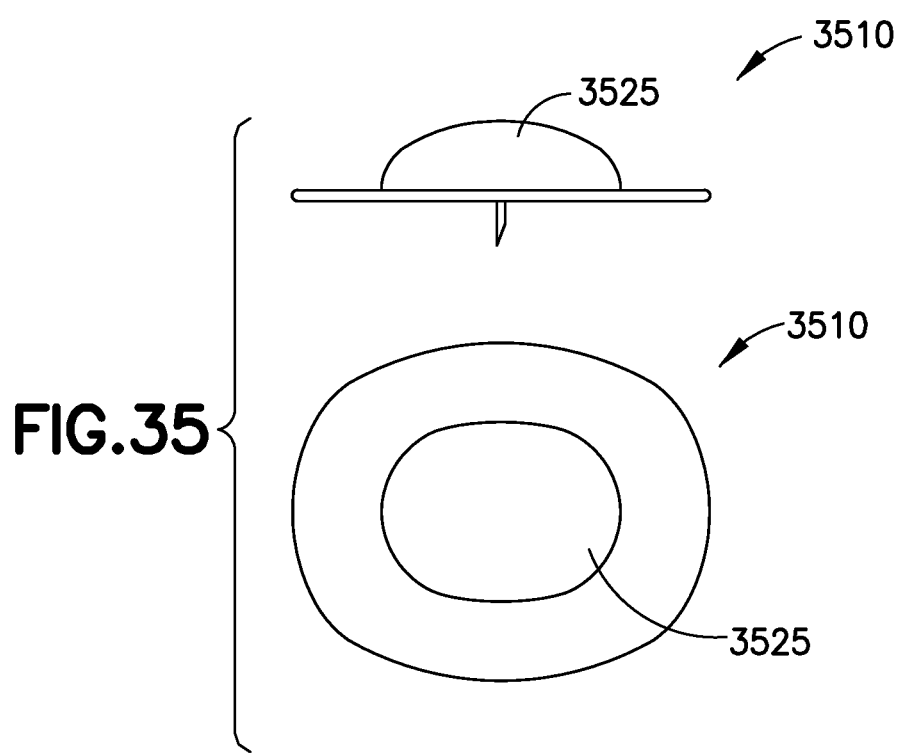
FIG. 35 shows another illustrative embodiment of an OBS device in accordance with the present invention, having a cover with no bumper portion and a low profile.

FIG. 35 shows an illustrative embodiment of an OBS 3510 having a cover 3525 with no bumper portion and a low profile. For example, the profile of the cover 3525 may be substantially 8 mm.

Figure 36:
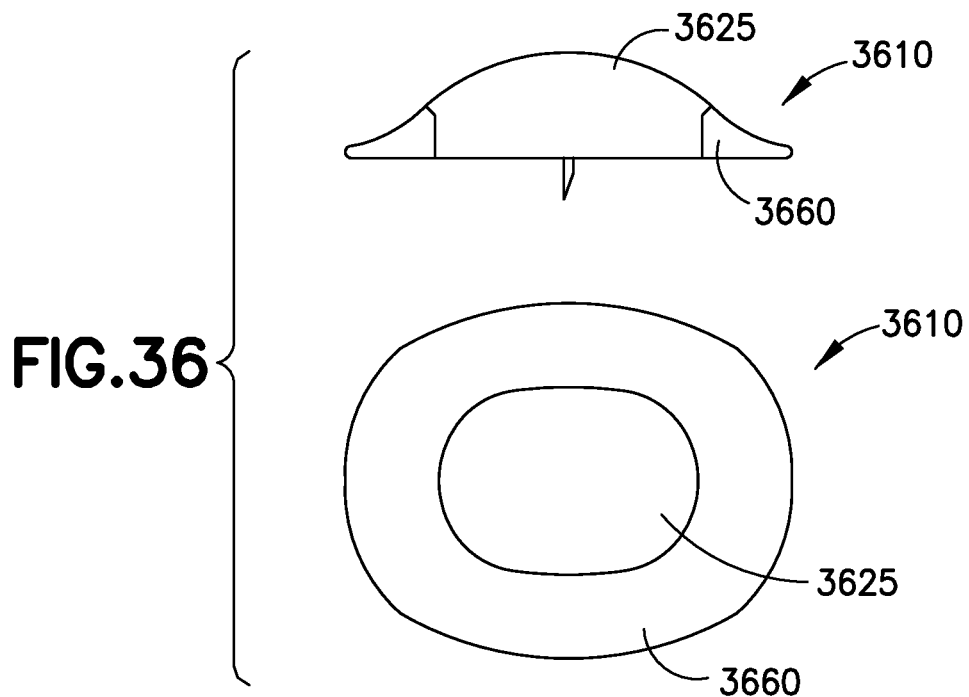
FIG. 36 shows an illustrative embodiment of an OBS having cover with a low profile.

FIG. 36 shows an illustrative embodiment of an OBS 3610 having a cover 3625 with a low profile. For example, the profile of the cover 3625 may be substantially 10 mm. OBS 3610 also includes a flange 3660 that slopes down from the cover 3625 to the outer perimeter of the flange 3660.

Figure 37:
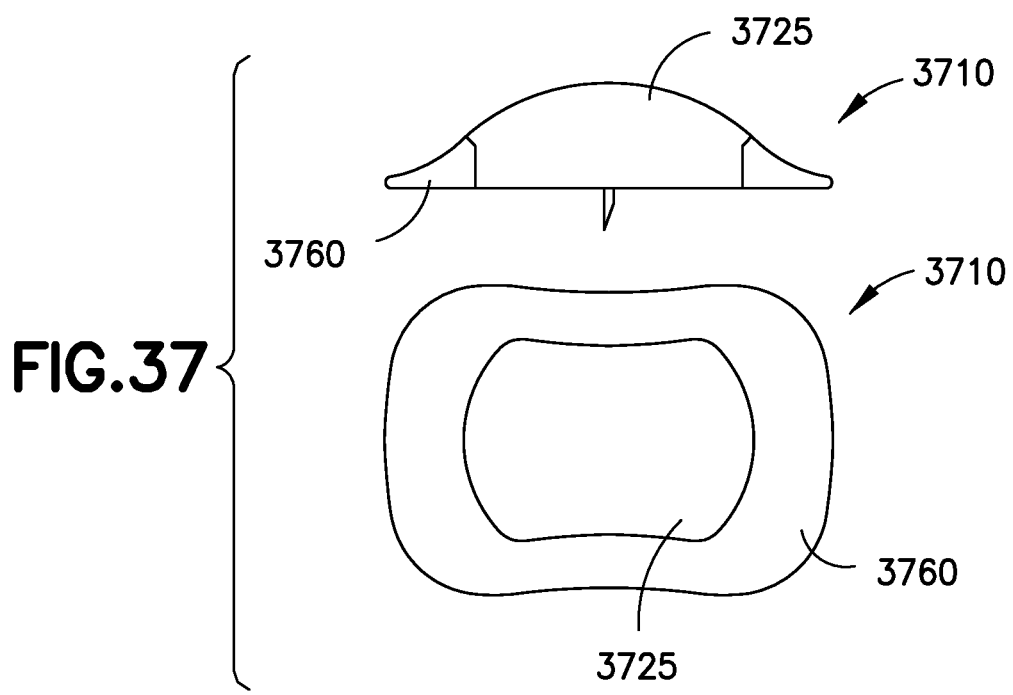
FIG. 37 shows another illustrative embodiment of an OBS device in accordance with the present invention, having a cover with a low profile.

FIG. 37 shows an illustrative embodiment of an OBS 3710 having a cover 3725 with a low profile. For example, the profile of the cover 3725 may be substantially 10 mm. OBS 3710 also includes a flange 3760 that slopes down from the cover 3725 to the outer perimeter of the flange 3760.

Figure 38:
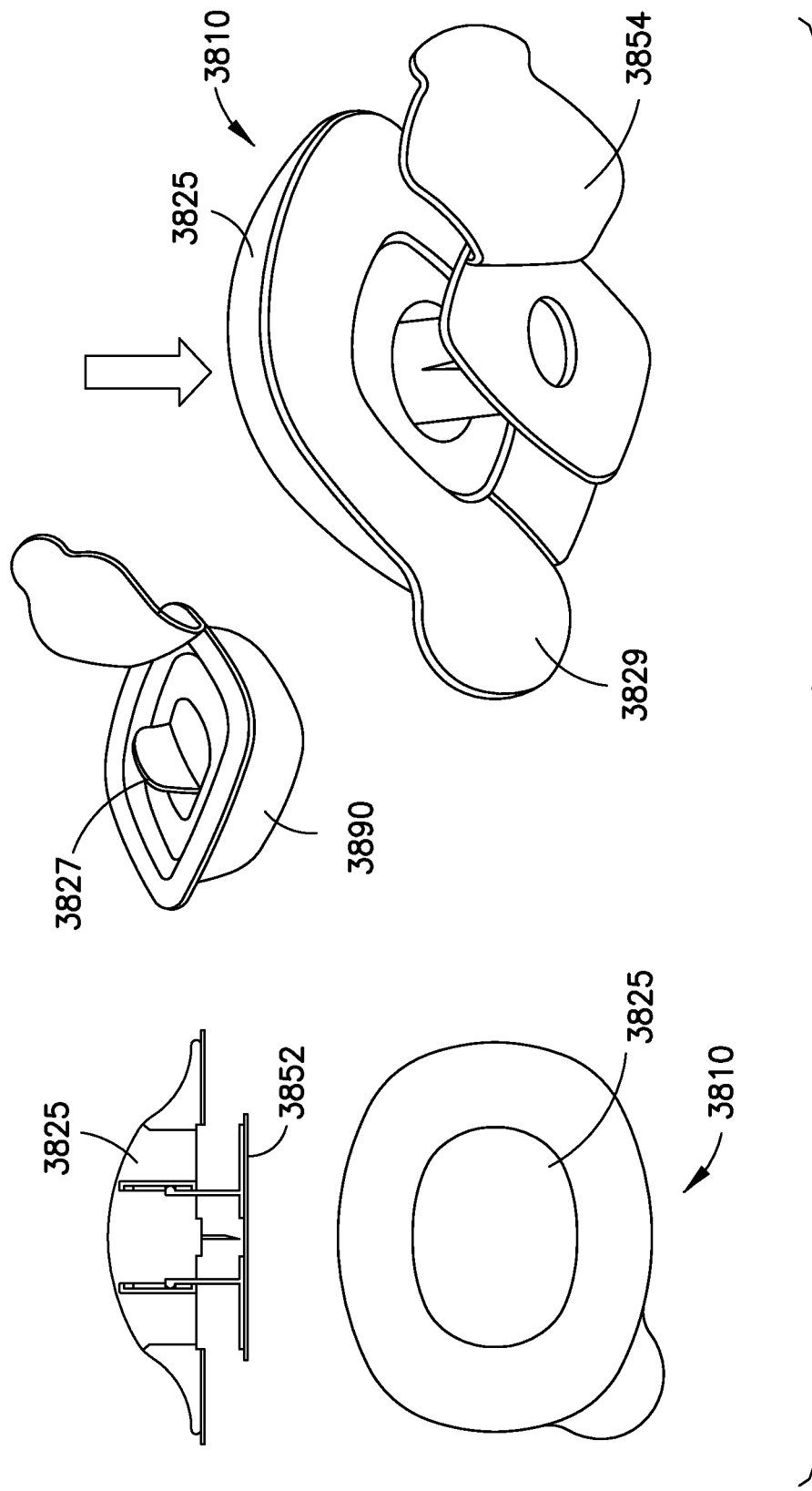
FIG. 38 shows another illustrative embodiment of an OBS device in accordance with the present invention, having a cover and an integrated needle inserter.

FIG. 38 shows an illustrative embodiment of an OBS 3810 having a cover 3825 and an integrated needle inserter 3852 that retracts into the cover 3825 during needle insertion. To apply the OBS 3810 a user can remove the OBS 3810 from a package 3890 using a handle 3827. Release paper 3829 and 3854 can then be removed, exposing an adhesive layer on the cover 3825 and the needle inserter 3852. The handle 3827 can then be folded down and a user can press down on the cover 3825 until the needle has been sufficiently inserted into the user and cover has been secured, via the adhesive, to the skin of the user.

FIG. 39 shows illustrative embodiments of OBS devices 3910A and 3910B having corresponding covers 3925A and 3925B. Cover 3925A is configured to receive a stabilizer 3973A having telescoping pins 3975A. Cover 3925B is configured to receive a stabilizer 3973B having a rotating sleeve 3977B which enables the cover 3925B to rotate with respect to the stabilizer 3973B during needle insertion such as, for example, needle insertion of needle 3930A. Covers 3925A and 3925B may also include a hinged handle 3927 and a pull cord 3979 which can be pulled to separate the OBS 3910A and 3910B from the user after use.

Figure 40:
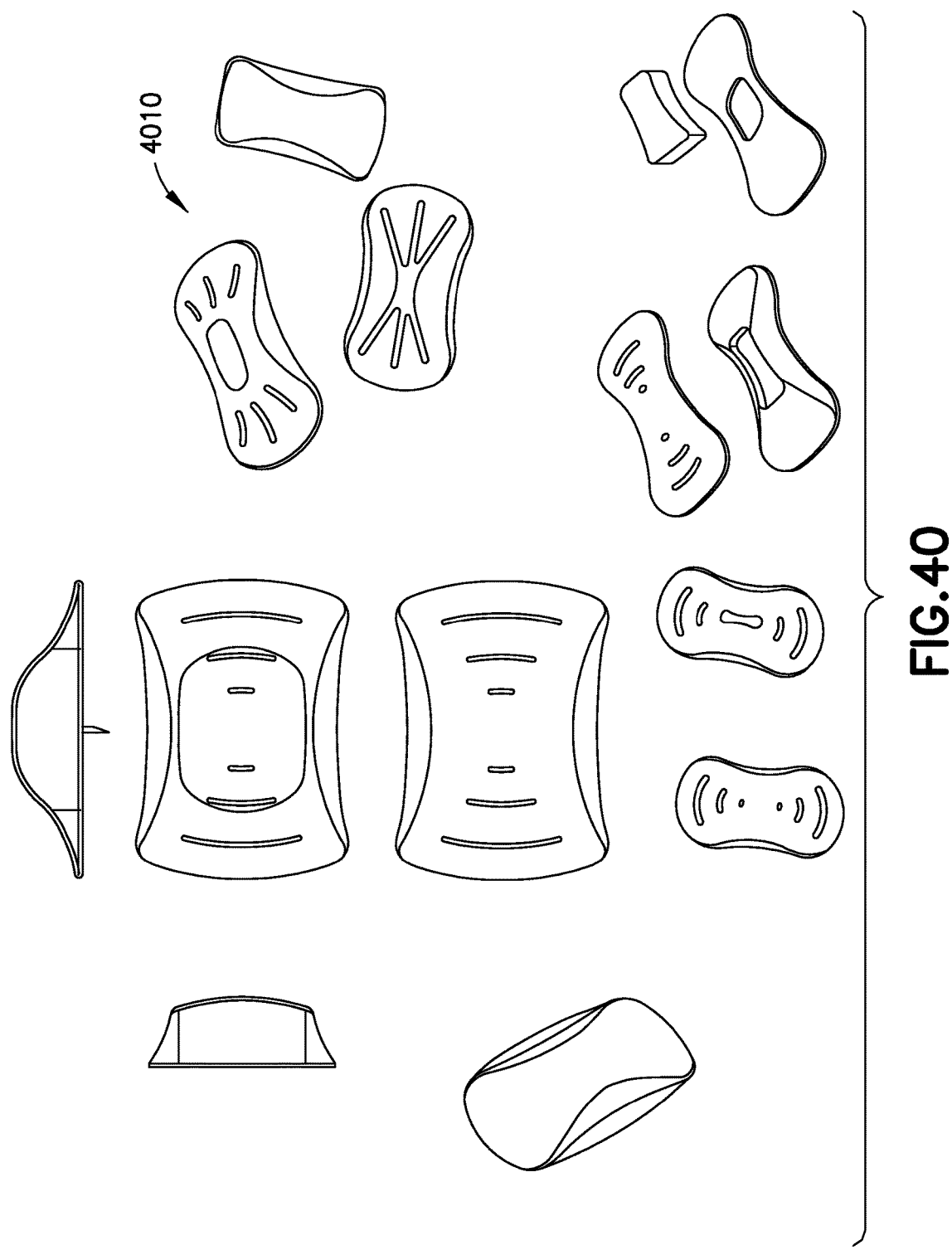
FIG. 40 shows another illustrative embodiment of an OBS device in accordance with the present invention, having scooped sides with exposed elastomer.

FIG. 40 shows illustrative embodiments of an OBS 4010 having scooped sides with exposed elastomer for easy handling and removal. The OBS 4010 can be formed with a silky fabric, non-woven laminate or other desired material.

Figure 41:
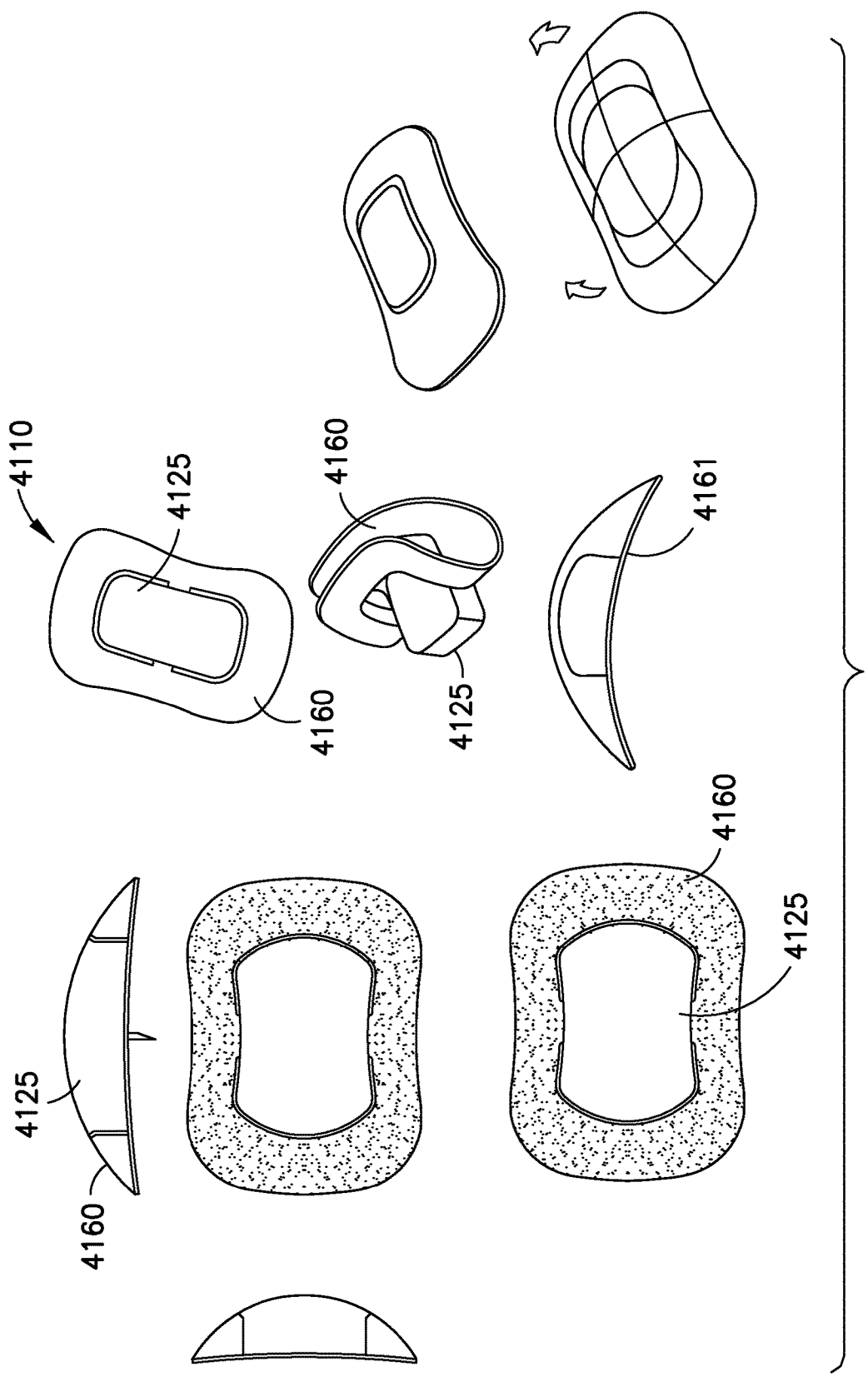
FIG. 41 shows another illustrative embodiment of an OBS device in accordance with the present invention, having a slight compound curved adhesive surface.

FIG. 41 shows an illustrative embodiment of an OBS 4110 having a cover 4125 and a flange 4160. The OBS 4110 has a slight compound curved adhesive surface 4161 to provide better comfort to the user during use. The top surface of the flange 4160 can include elastomeric bumps for improved grip during positioning and removal of the OBS 4110. To remove the OBS 4110, a user can lift opposing sides of the flange 4160 that separate from the cover 4125 and lift the OBS 4110 off of the user.

Figure 42:
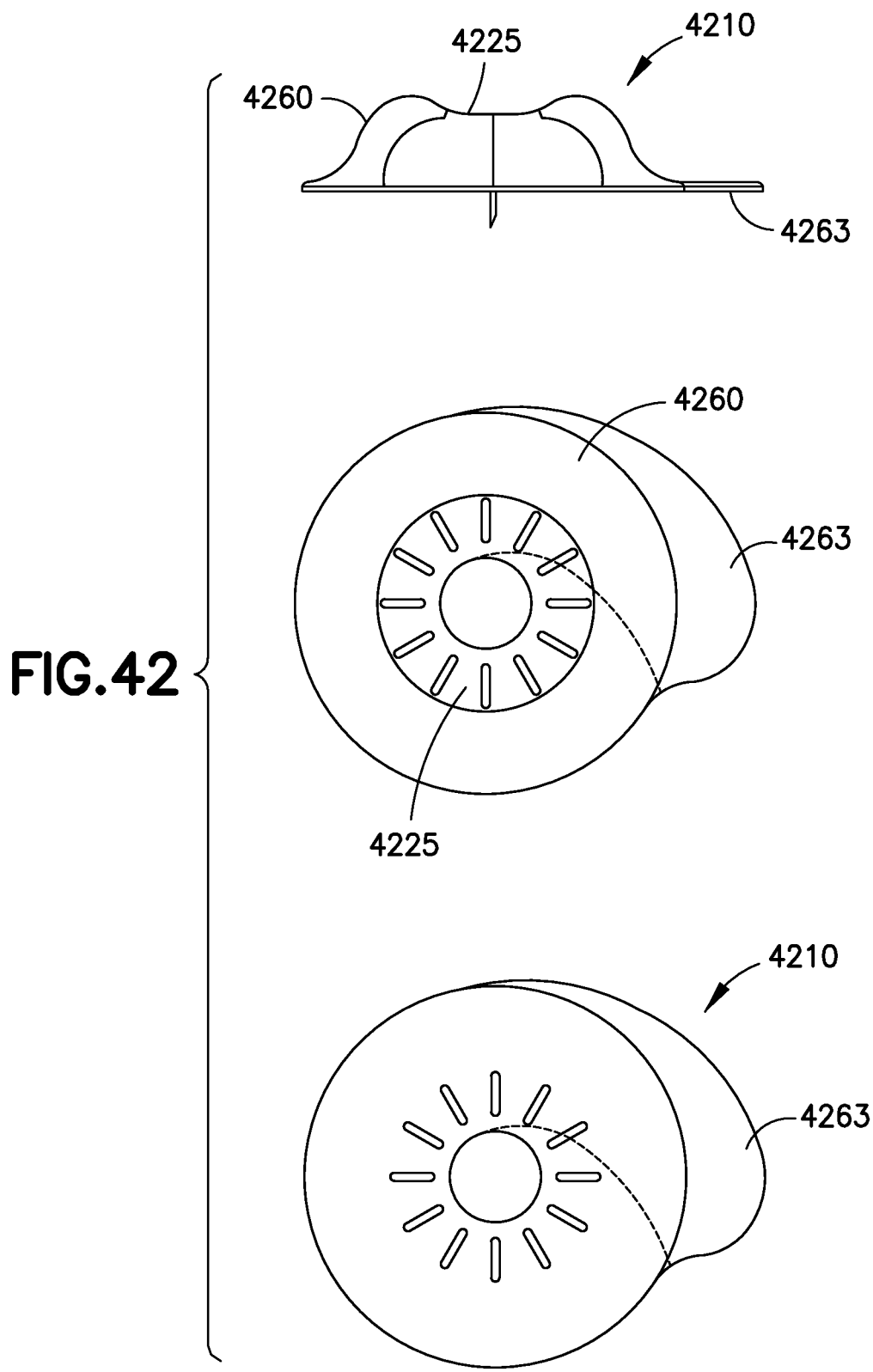
FIG. 42 shows another illustrative embodiment of an OBS device in accordance with the present invention, having a substantially annular shape.

FIG. 42 shows an illustrative embodiment of an OBS 4210 having a substantially annular shape. The OBS 4210 includes a cover 4225 and a flange 4260. The flange 4260 has a slightly higher profile than the cover, enabling the flange to absorb minor impact without impacting the cover 4225. The flange 4260 can be made of a foam-like material and has a slightly asymmetrical shape due to a removal tape 4263 on a bottom surface of the flange 4260. To remove the OBS 4210 from the user, the remove tape 4263 can be lifted, thereby releasing the OBS 4210 from the user. The OBS 4210 can also include a smooth radial exterior surface to more effectively glide over a user's clothes during use.

Figure 43:
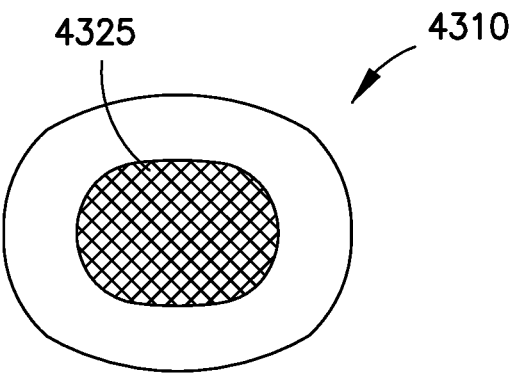
FIG. 43 shows another illustrative embodiment of an OBS device in accordance with the present invention, having a cover with a lattice design.

FIG. 43 shows an illustrative embodiment of an OBS 4310 including a cover 4325 having a lattice design to improve grip and aesthetic design of the OBS 4310.

Figure 44:
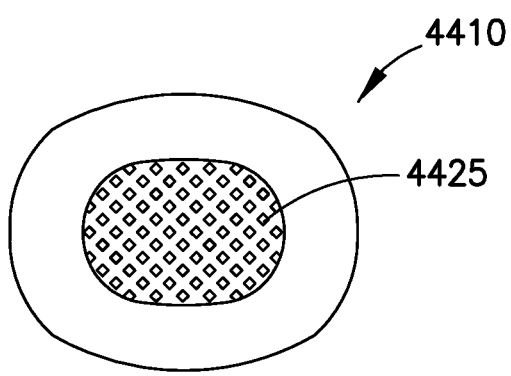
FIG. 44 shows another illustrative embodiment of an OBS device in accordance with the present invention, having a cover with an overlapping square design.

FIG. 44 shows an illustrative embodiment of an OBS 4410 including a cover 4425 having an overlapping square design to improve grip and aesthetic design of the OBS 4410.

Figure 45:
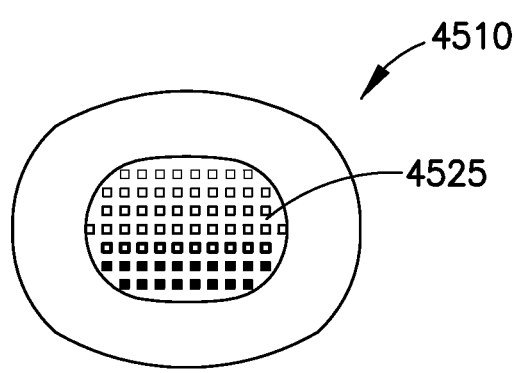
FIG. 45 shows another illustrative embodiment of an OBS device in accordance with the present invention, having a cover with a fading grip pattern.

FIG. 45 shows an illustrative embodiment of an OBS 4510 including a cover 4525 having a fading grip pattern design to improve grip and aesthetic design of the OBS 4510.

Figure 46:
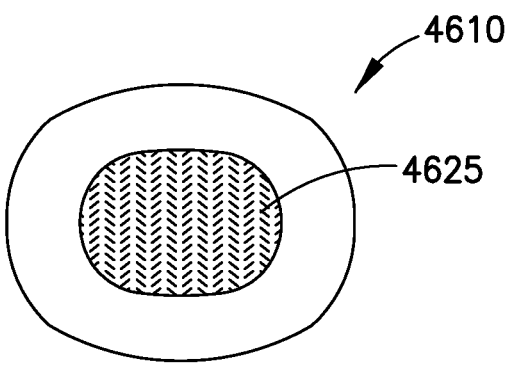
FIG. 46 shows another illustrative embodiment of an OBS device in accordance with the present invention, having a cover with a knit pattern design.

FIG. 46 shows an illustrative embodiment of an OBS 4610 including a cover 4625 having a knit pattern design to improve grip and aesthetic design of the OBS 4610.

Figure 47:
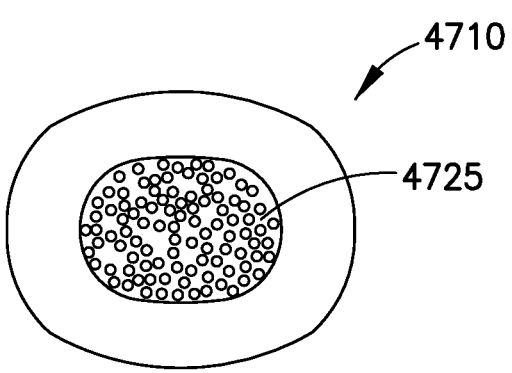
FIG. 47 shows another illustrative embodiment of an OBS device in accordance with the present invention, having a cover with a random dots pattern.

FIG. 47 shows an illustrative embodiment of an OBS 4710 including a cover 4725 having a random dots pattern to improve grip and aesthetic design of the OBS 4710.

Figure 48:
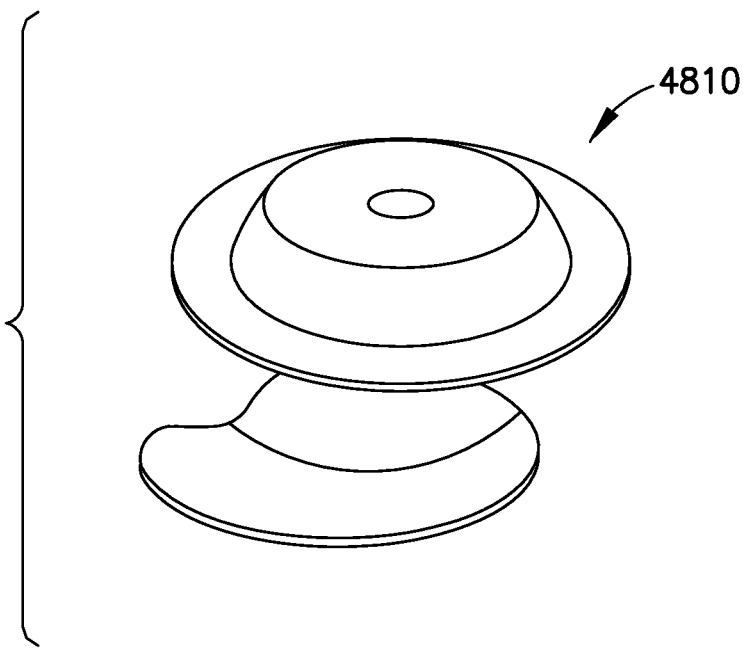
FIG. 48 shows another illustrative embodiment of an OBS device in accordance with the present invention, having an annular shape.

FIG. 48 shows an illustrative embodiment of an OBS 4810 having an annular shape.

Figure 49:
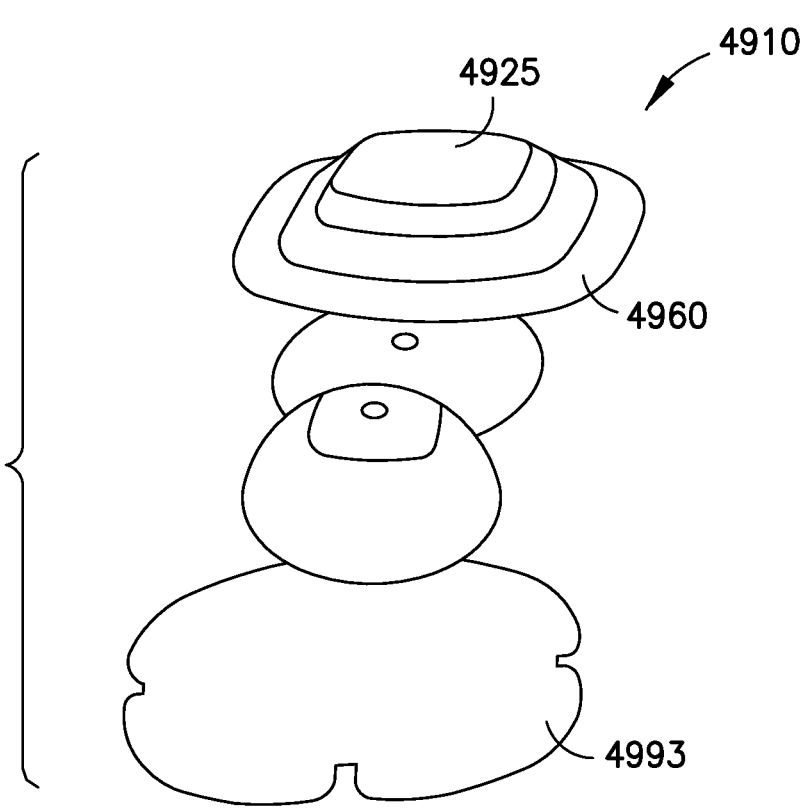
FIG. 49 shows another illustrative embodiment of an OBS device in accordance with the present invention, having a square-shaped cover and a slightly elongated soft flange.

FIG. 49 shows an illustrative embodiment of an OBS 4910 having square-shaped cover 4925 and a slightly elongated soft flange 4960. The OBS 4910 also includes flat adhesive petals 4993 around the perimeter of the OBS 4910.

Figure 50:
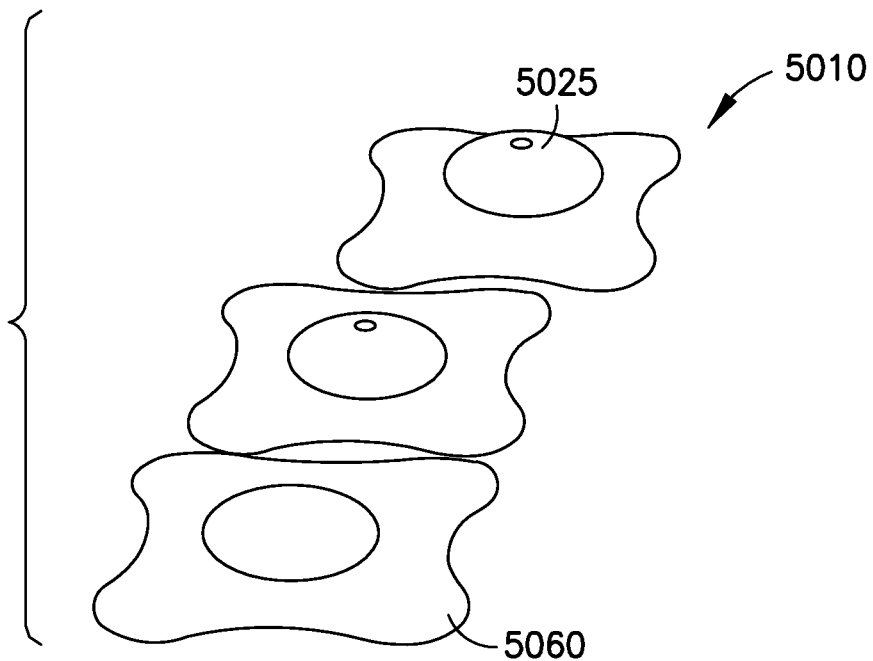
FIG. 50 shows another illustrative embodiment of an OBS device in accordance with the present invention, having a cover and a pinwheel-shaped flange.

FIG. 50 shows an illustrative embodiment of an OBS 5010 having a cover 5025 and a pinwheel-shaped flange 5060. The OBS 5010 also includes a fabric bandage material adhesive to add comfort and flexibility to the user during use.

Figure 51:
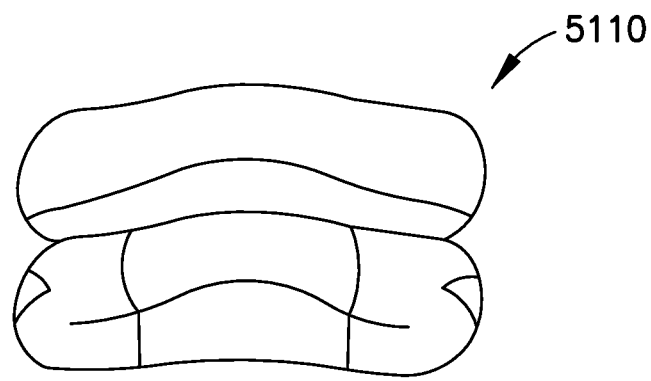
FIG. 51 shows another illustrative embodiment of an OBS device in accordance with the present invention, having a substantially hourglass-like shape.

FIG. 51 shows an illustrative embodiment of an OBS 5110 that having a substantially hourglass-like shape and including a soft material over the gripping area to provide improved handling by the user. A fabric bandage can also be used to cover the whole surface of the OBS 5110.

Figure 52:
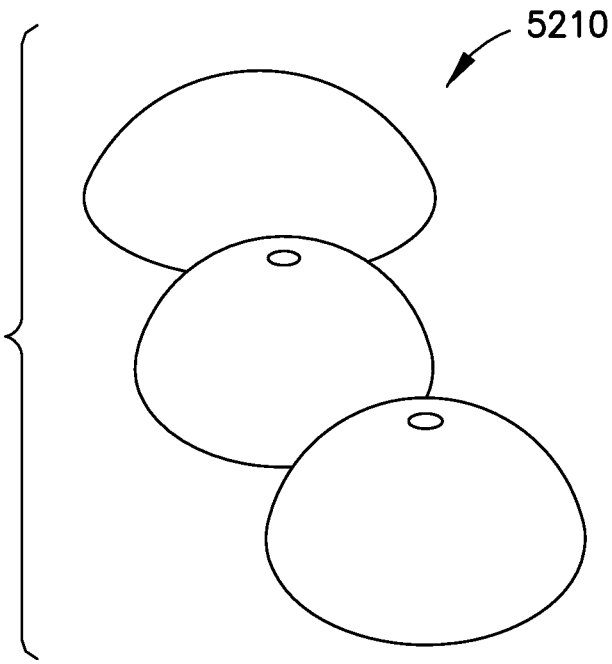
FIG. 52 shows another illustrative embodiment of an OBS device in accordance with the present invention, having a domed ellipse shape.

FIG. 52 shows an illustrative embodiment of an OBS 5210 having domed ellipse shape.

Figure 53:
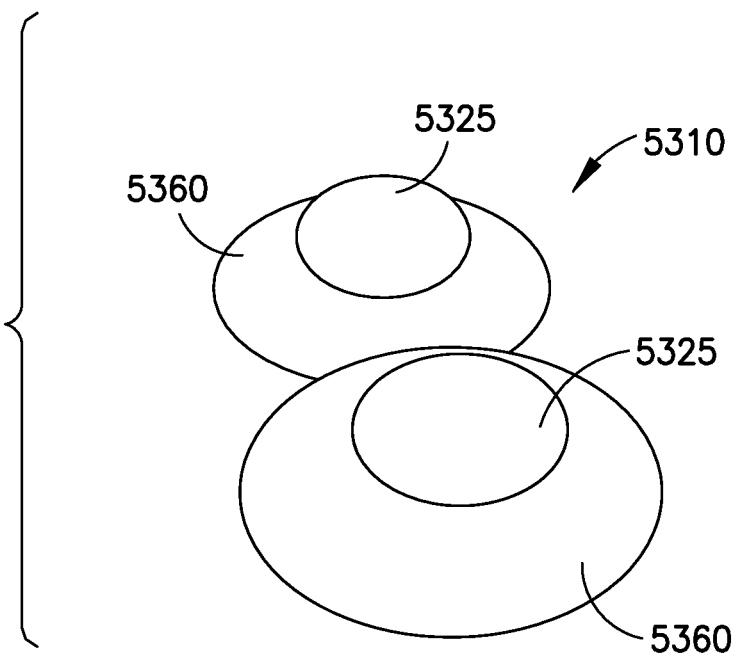
FIG. 53 shows another illustrative embodiment of an OBS device in accordance with the present invention, having a cover and a concave flange.

FIG. 53 shows an illustrative embodiment of an OBS 5310 having a cover 5325 and a concave flange 5360. Alternatively a convex flange can also be used.

Figure 54:
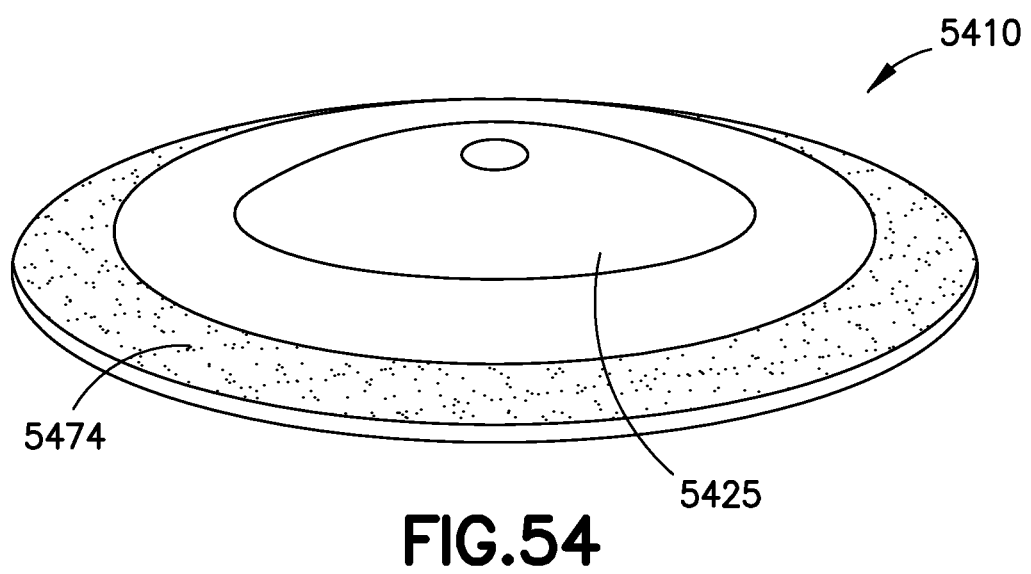
FIG. 54 shows another illustrative embodiment of an OBS device in accordance with the present invention, having a cover mounted on a foam layer ring.

FIG. 54 shows an illustrative embodiment of an OBS 5410 having a cover 5425 mounted on a foam layer ring 5474 to provide improved flexibility during use.

FIGS. 55A-55C shows illustrative embodiments of OBS devices 5510A-C having corresponding covers 5525A-C and application assemblies 5595A-C.

With respect to FIG. 55A, during application a user begins by removing a cap 5570A that includes a sponge, the cap 5570A covering a needle of the OBS 5510A. The user then removes an adhesive backer 5572A that exposes an adhesive that secures the OBS 5510A to the skin of the user. Next, the user inserts the needle by pushing on the pin 5575A. Then the user removes another adhesive backer 5588A that exposes an adhesive on the top surface of the OBS 5510A. Next, the user removes a protection tube 5589A which protects the pin 5575A from damage and houses an OBS cover material 5586A. As the tube 5589A is removed the cover material 5586A is released and can be positioned by the user over the exposed adhesive on the OBS 5510A. Lastly, the pin 5575A can be removed which can start a battery in the OBS 5510A.

With respect to FIG. 55B, during application a user inserts the needle by pushing on the pin 5575B. Then the user removes an adhesive backer 5588B that exposes an adhesive on the top surface of the OBS 5510B. Next, the user removes a protection tube 5589B which protects the pin 5575B from damage and houses an OBS cover material 5586B. As the tube 5589B is removed the cover material 5586B is released and can be positioned by the user over the exposed adhesive on the OBS 5510B. Lastly, the pin 5575B can be removed which can start a battery in the OBS 5510B.

With respect to FIG. 55C, during application a user inserts the needle by pushing on the pin 5575C. Then the user removes an adhesive backer 5588C that exposes an adhesive on the top surface of the OBS 5510C. Next, the user removes a protection tube 5589C which protects the pin 5575C from damage and houses an OBS cover material 5586C. As the tube 5589C is removed the cover material 5586C is released and can be positioned by the user over the exposed adhesive on the OBS 5510C. Lastly, the pin 5575C can be removed which can start a battery in the OBS 5510C.

Figure 56:
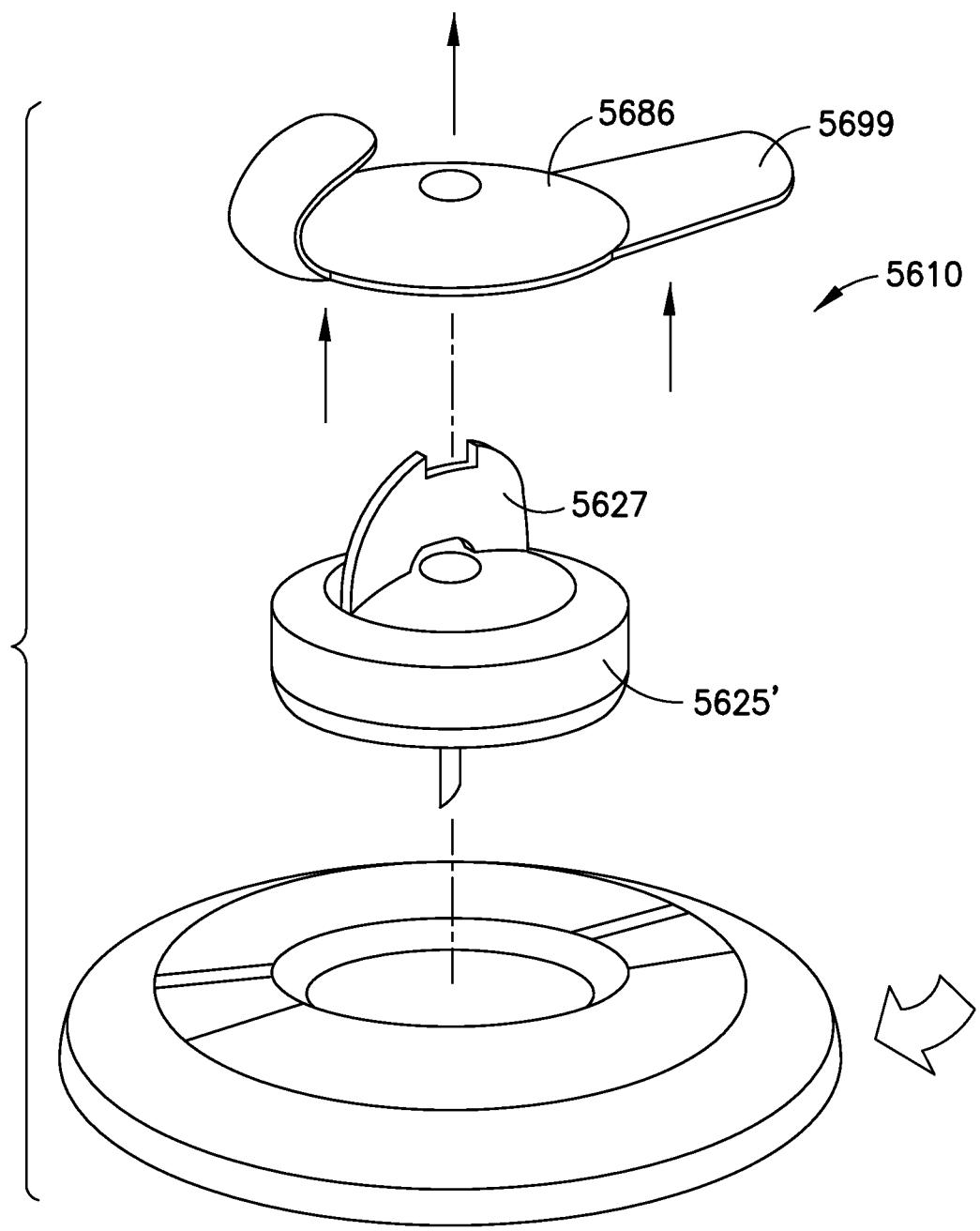
FIG. 56 shows an illustrative embodiment of an OBS and an illustrative embodiment of a removal method for an illustrative embodiment of an OBS.

FIG. 56 shows an illustrative embodiment of an OBS 5610 and a removal method for removing the OBS 5610 from the user. The OBS can be removed by first pulling on tabs 5699 integral with a cover material 5686. Pulling on the tabs 5699 releases the cover material from the top surface of the OBS housing 5625'. Next, the user can pull a handle 5627 which release the OBS housing 5625' from the user. Lastly, a foam layer can be peeled away from the user and removed.

Figure 57:
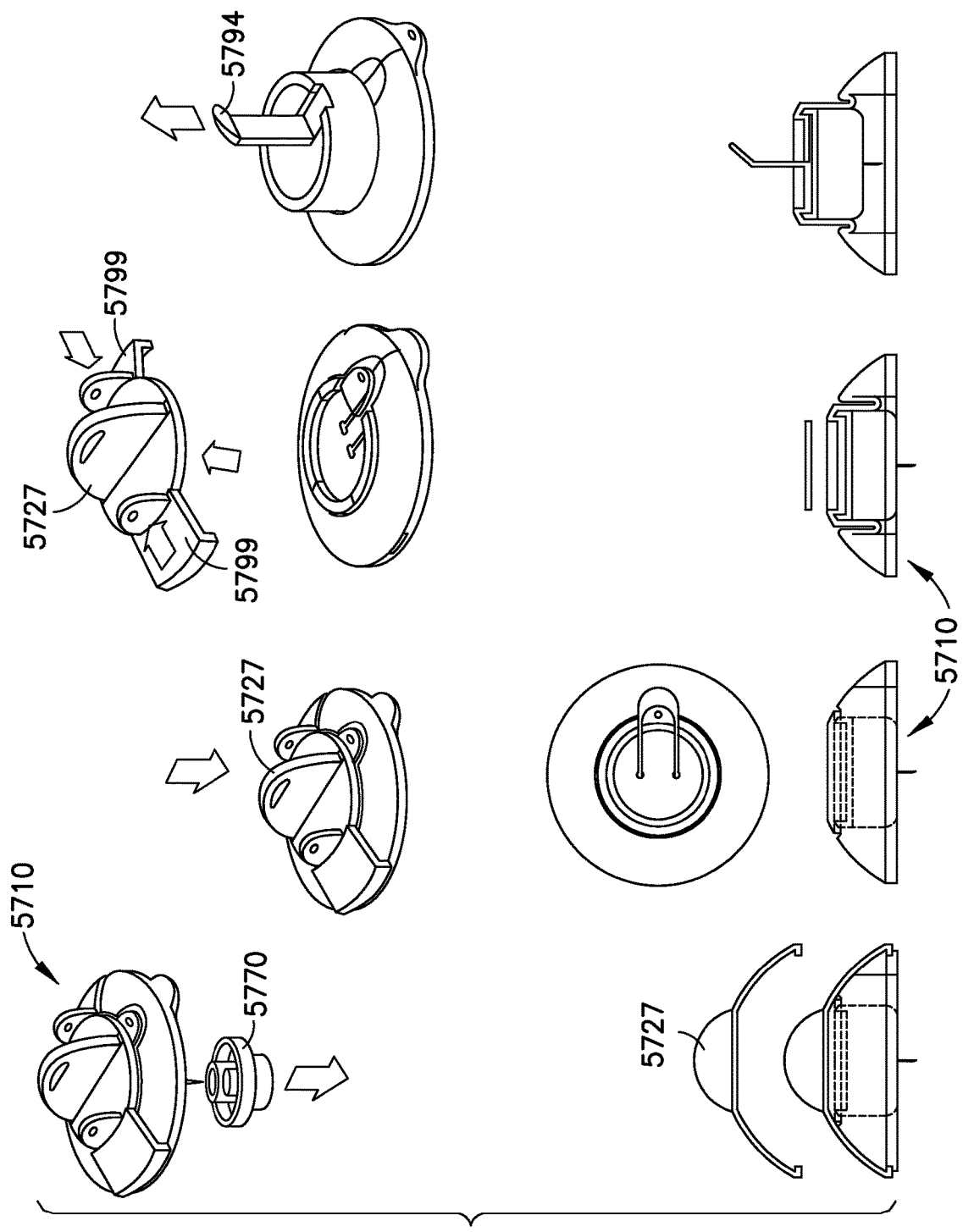
FIG. 57 shows an illustrative embodiment of an OBS and an illustrative embodiment of an application and removal method for an illustrative embodiment of an OBS.

FIG. 57 shows an illustrative embodiment of an OBS 5710 and an application and removal method. First, a needle cap 5770, having a sponge, and an adhesive backer is removed from an underside of the OBS 5710. The OBS 5710 is then secured to the skin of the user and the needle is inserted by applying downward pressure on a handle 5727. A user can then apply opposing forces to release tabs 5799 on the handle 5727, which releases the handle 5727 from the body of the OBS 5710 providing a lower profile OBS 5710. After use, a user can pull up on an elastomer tab 5794, which removes the needle from the user. Lastly, the user can peel the OBS 5710 away from the skin of the user and remove the OBS 5710.

Figure 58:
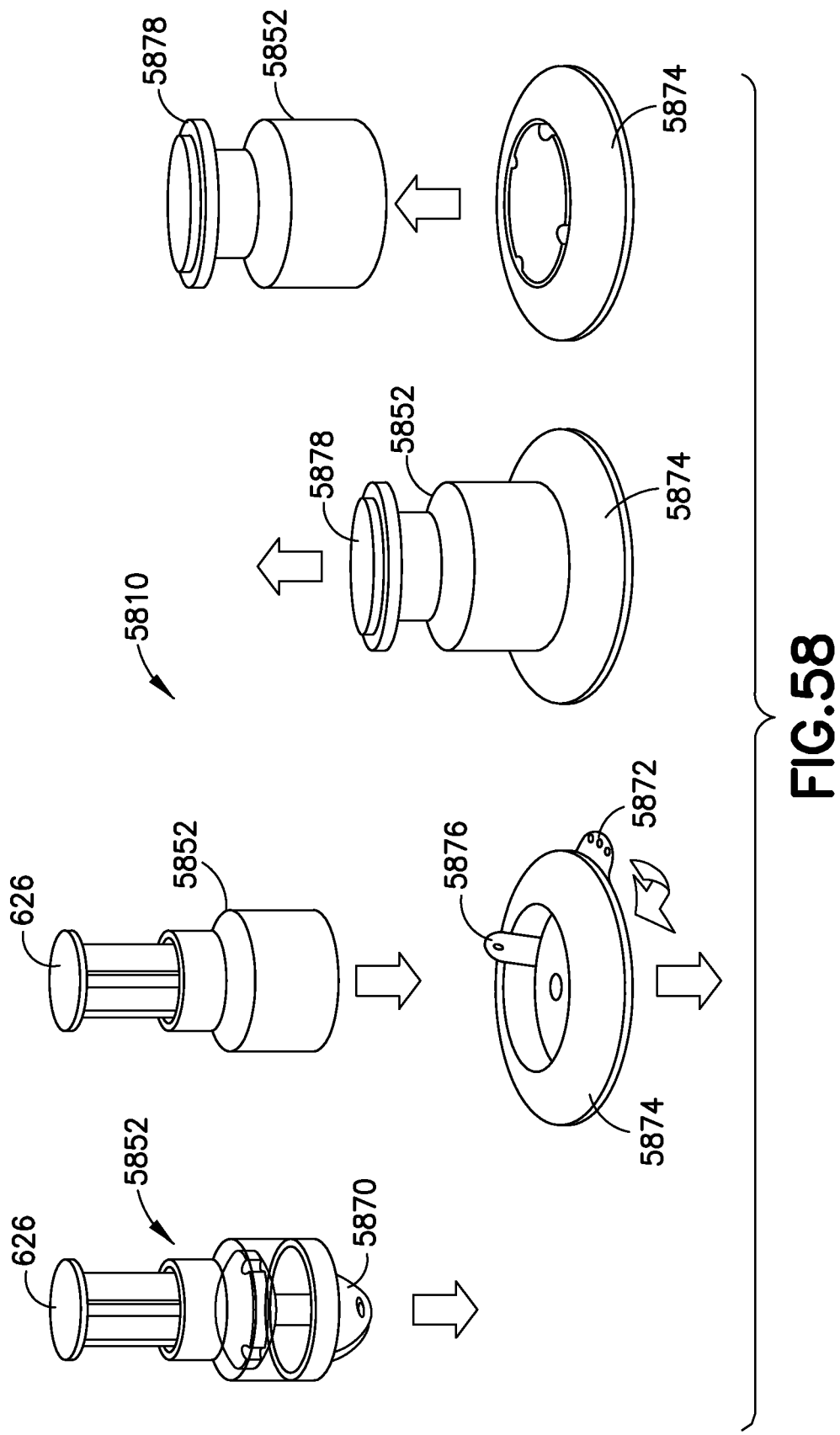
FIG. 58 shows an illustrative embodiment of an OBS and an illustrative embodiment of an application method for an illustrative embodiment of an OBS.

FIG. 58 shows an illustrative embodiment of an OBS 5810 and application method. To apply the OBS 5810 to a user, first, a needle cap 5870, having a sponge, is removed from an inserter assembly 5852. Then, an adhesive backer 5872 is removed from the underside of a foam layer 5874 and the foam layer 5874 is secured to the skin of the user. A second adhesive backer 5876 is removed on an interior surface of the foam layer 5874 which allows the OBS 5810 to bond to the user via the foam layer 5874. The user can then align the inserter assembly 5852 within the foam layer 5874 and plunge the OBS 5810 into the foam layer 5874 using a plunger rod 5878. The user can then pull up on the inserter assembly 5852 and remove the inserter assembly from the OBS 5810.

Figure 59:
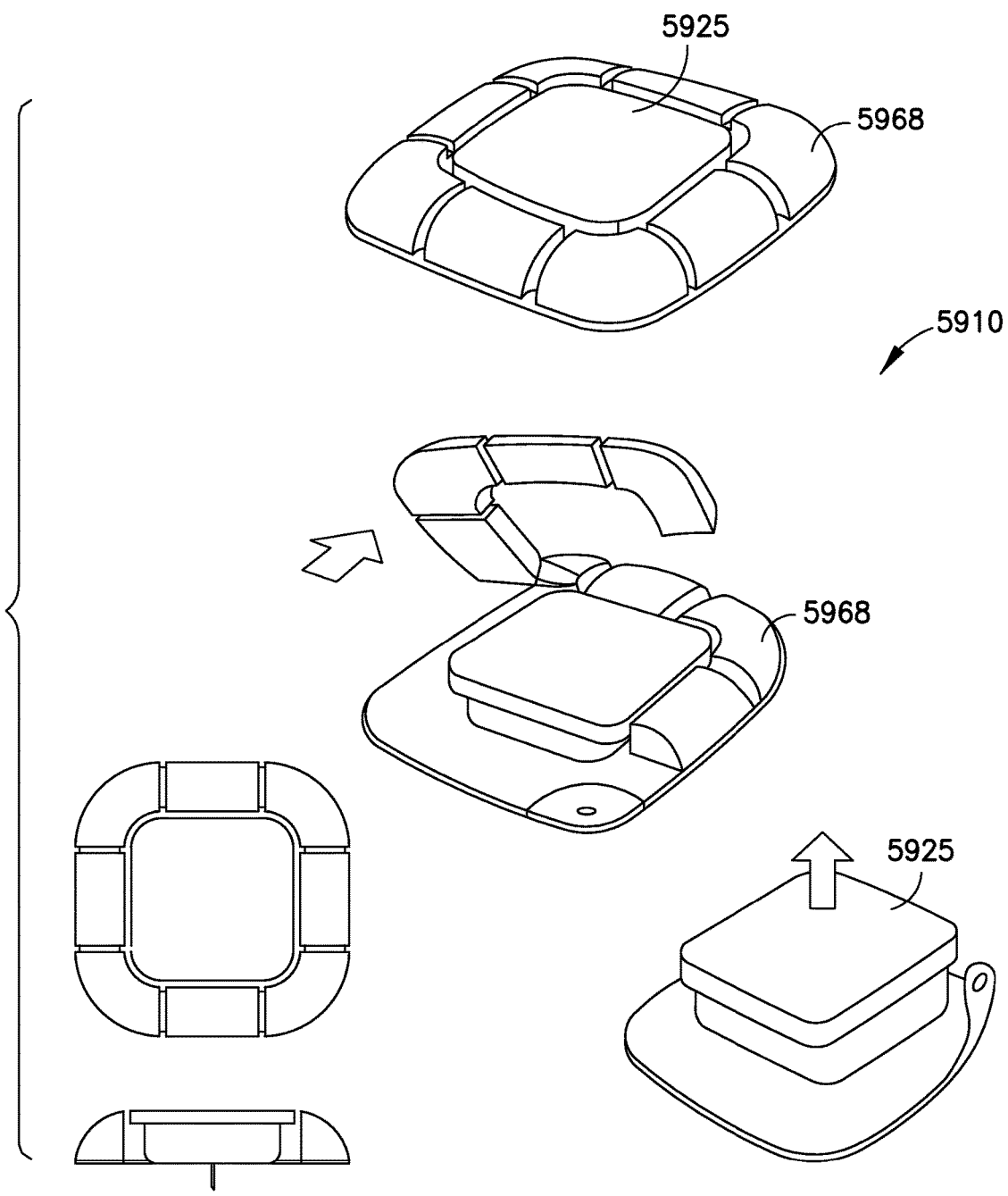
FIG. 59 shows another illustrative embodiment of an OBS device in accordance with the present invention, having a removable segmented foam layer.

FIG. 59 shows an illustrative embodiment of an OBS 5910 having a cover 5925 and a removable foam layer 5968.

Figure 60:
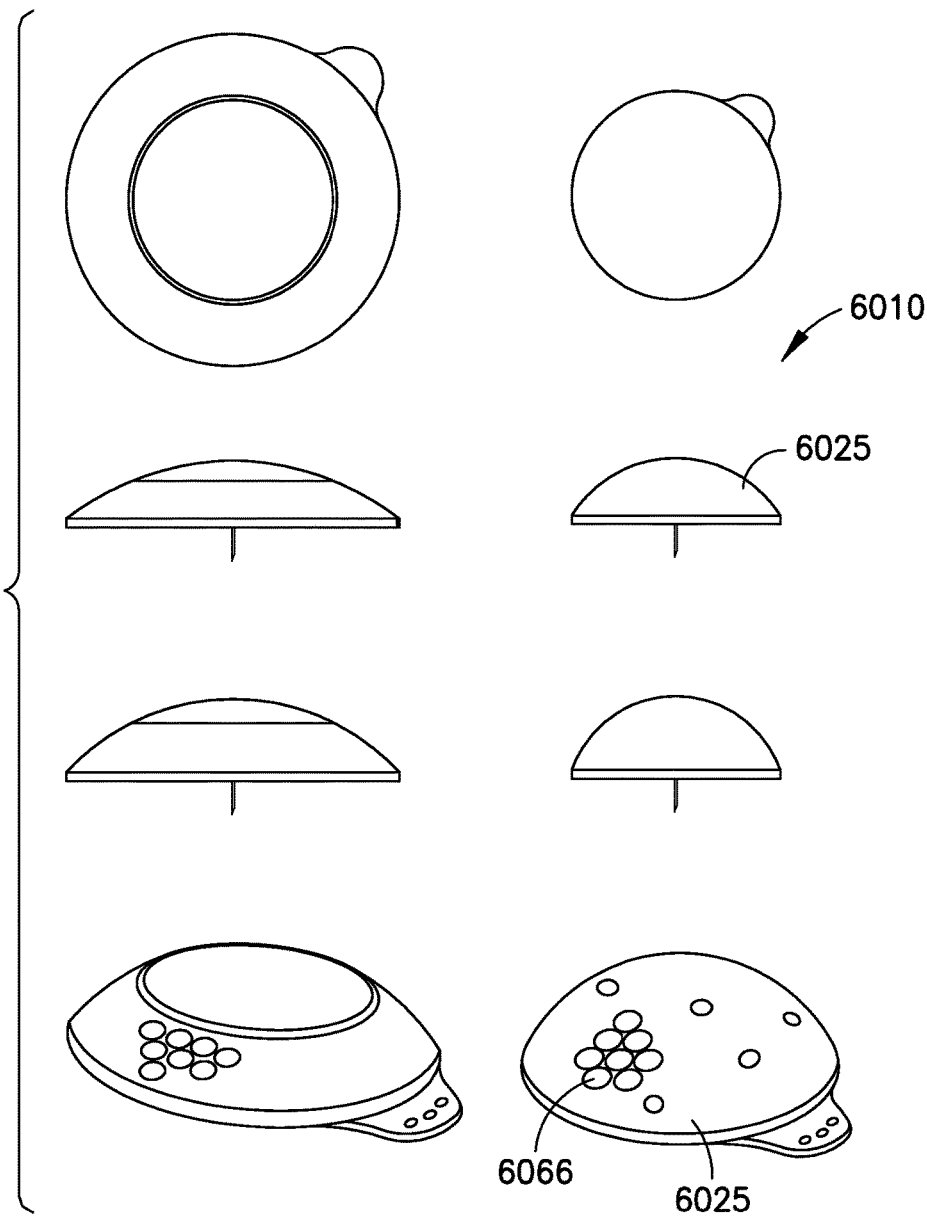
FIG. 60 shows another illustrative embodiment of an OBS device in accordance with the present invention, having a cover with elastomer nodules.

FIG. 60 shows an illustrative embodiment of an OBS 6010 including a cover 6025 having elastomer nodules 6066 to provide grip during handling and reduce surface area and friction with clothing.

Figure 61:
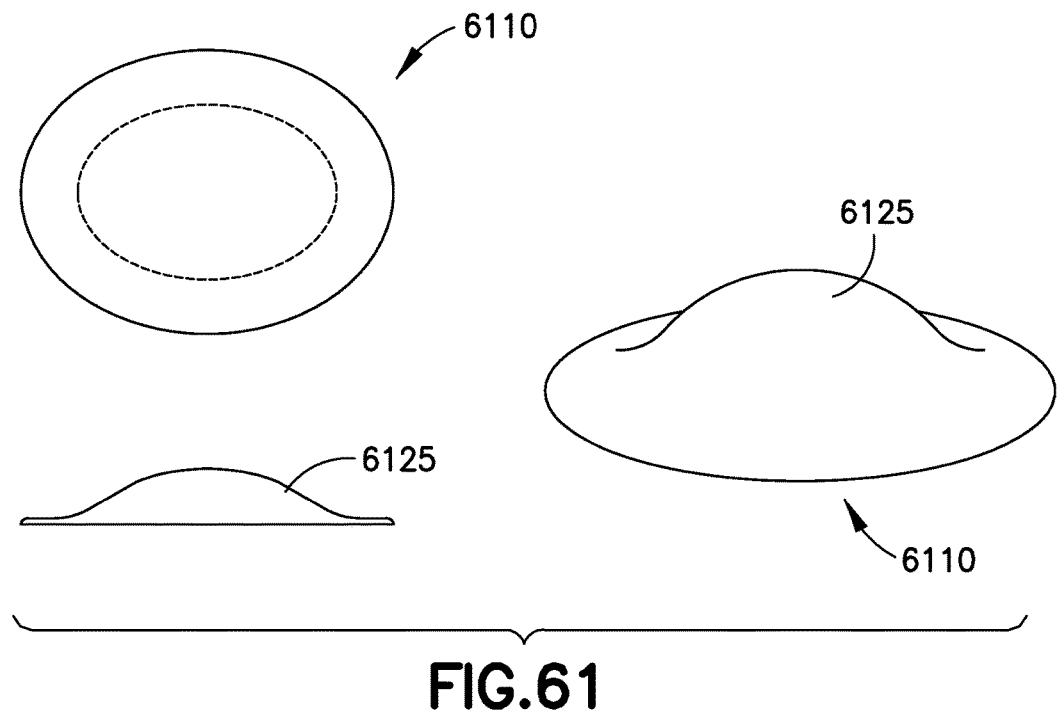
FIG. 61 shows another illustrative embodiment of an OBS device in accordance with the present invention, having a unitary, soft, flexible cover.

FIG. 61 shows an illustrative embodiment of an OBS 6110 having a unitary, soft, flexible cover 6125.

Figure 62:
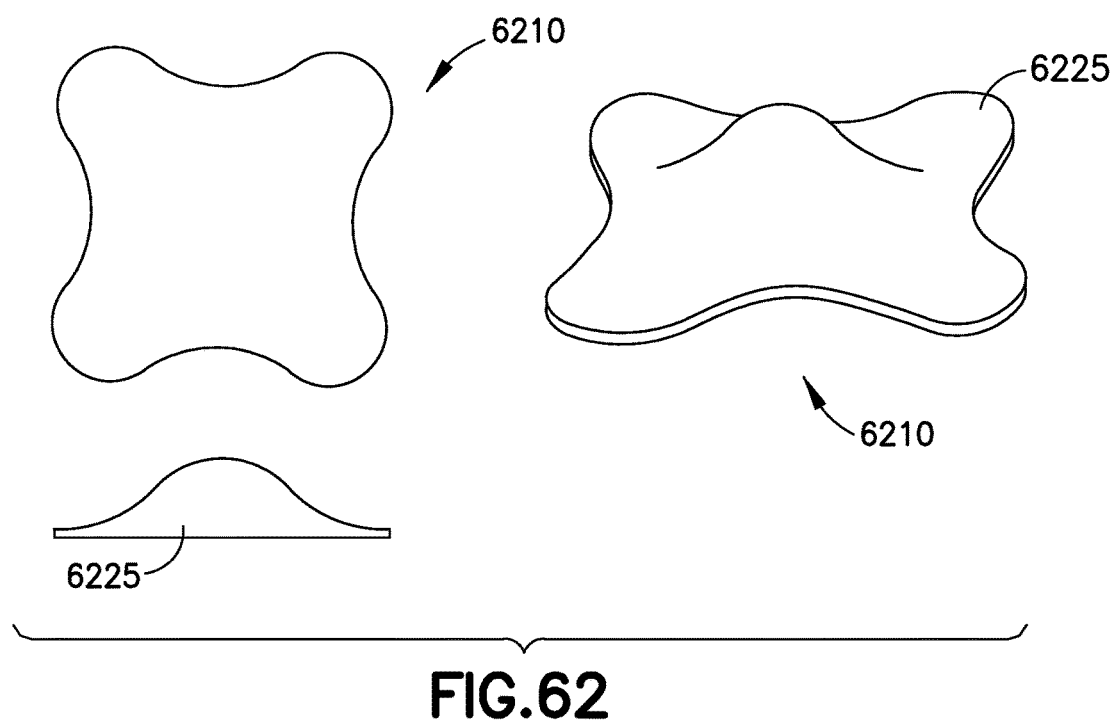
FIG. 62 shows another illustrative embodiment of an OBS device in accordance with the present invention, having a unitary cover having a substantially pinwheel shape.

FIG. 62 shows an illustrative embodiment of an OBS 6210 including a unitary cover 6225 having a substantially pinwheel shape.

Figure 63:
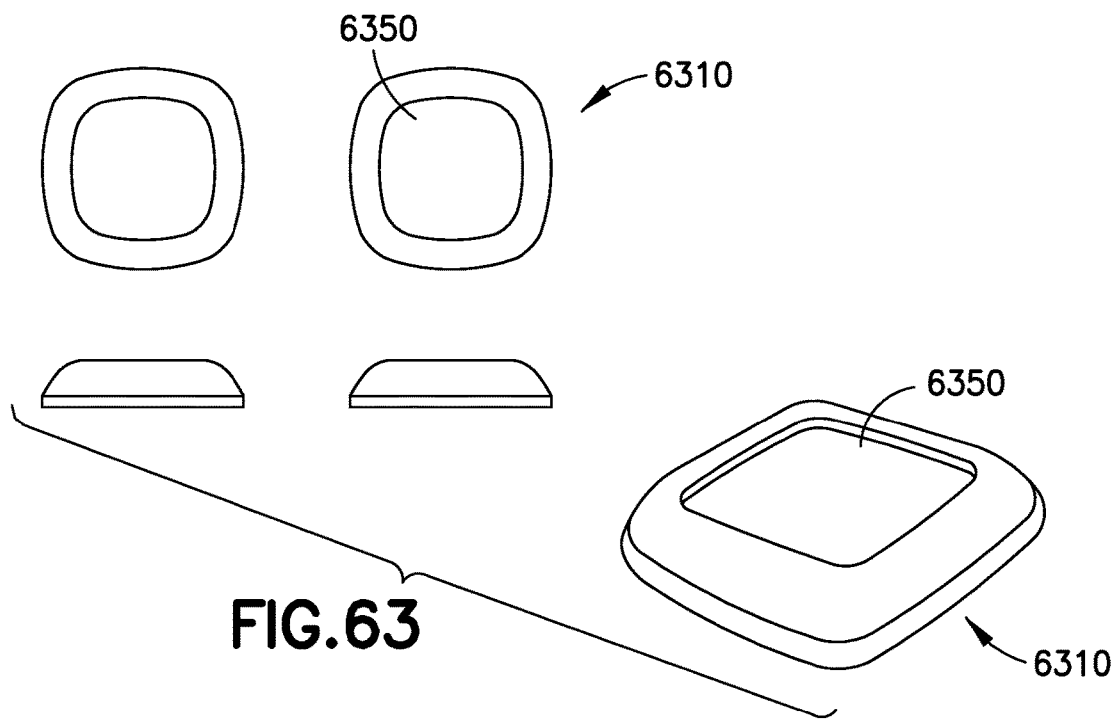
FIG. 63 shows another illustrative embodiment of an OBS device in accordance with the present invention, having a recessed center portion.

FIG. 63 shows an illustrative embodiment of an OBS 6310 having a recessed center portion 6350.

Figure 64:
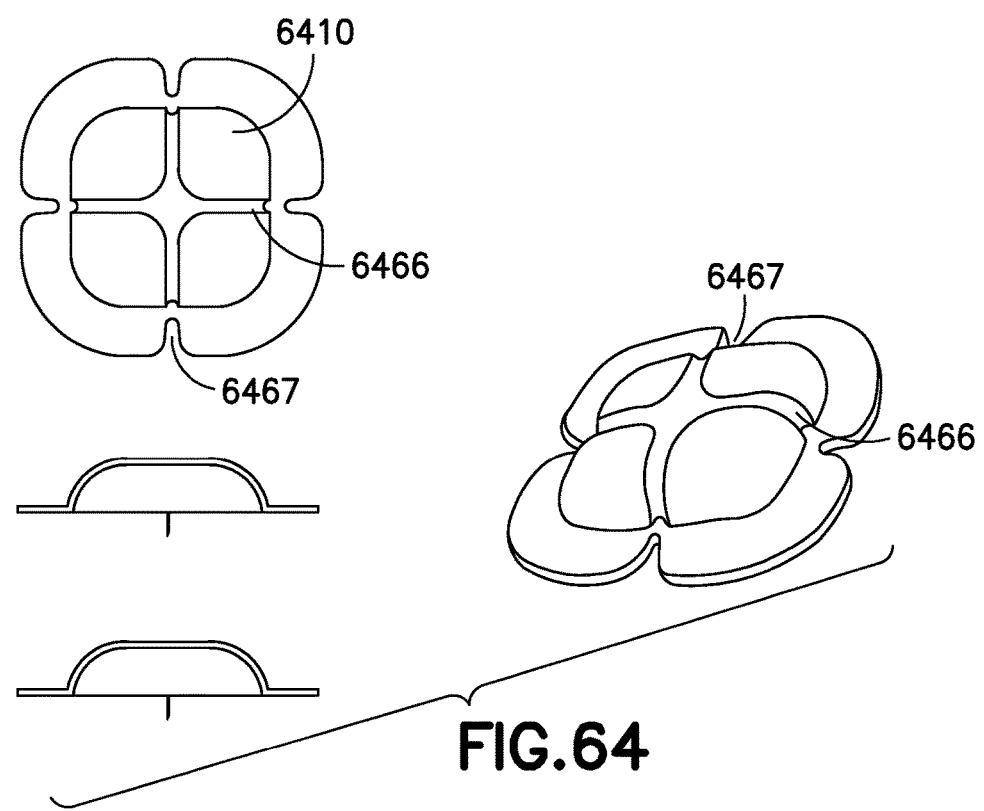
FIG. 64 shows another illustrative embodiment of an OBS device in accordance with the present invention, having a flex zone.

FIG. 64 shows an illustrative embodiment of an OBS 6410 having flex zones 6466 and 6467 where the OBS 6410 can flex and conform to the user, thereby increasing comfort to the user.

Figure 65:
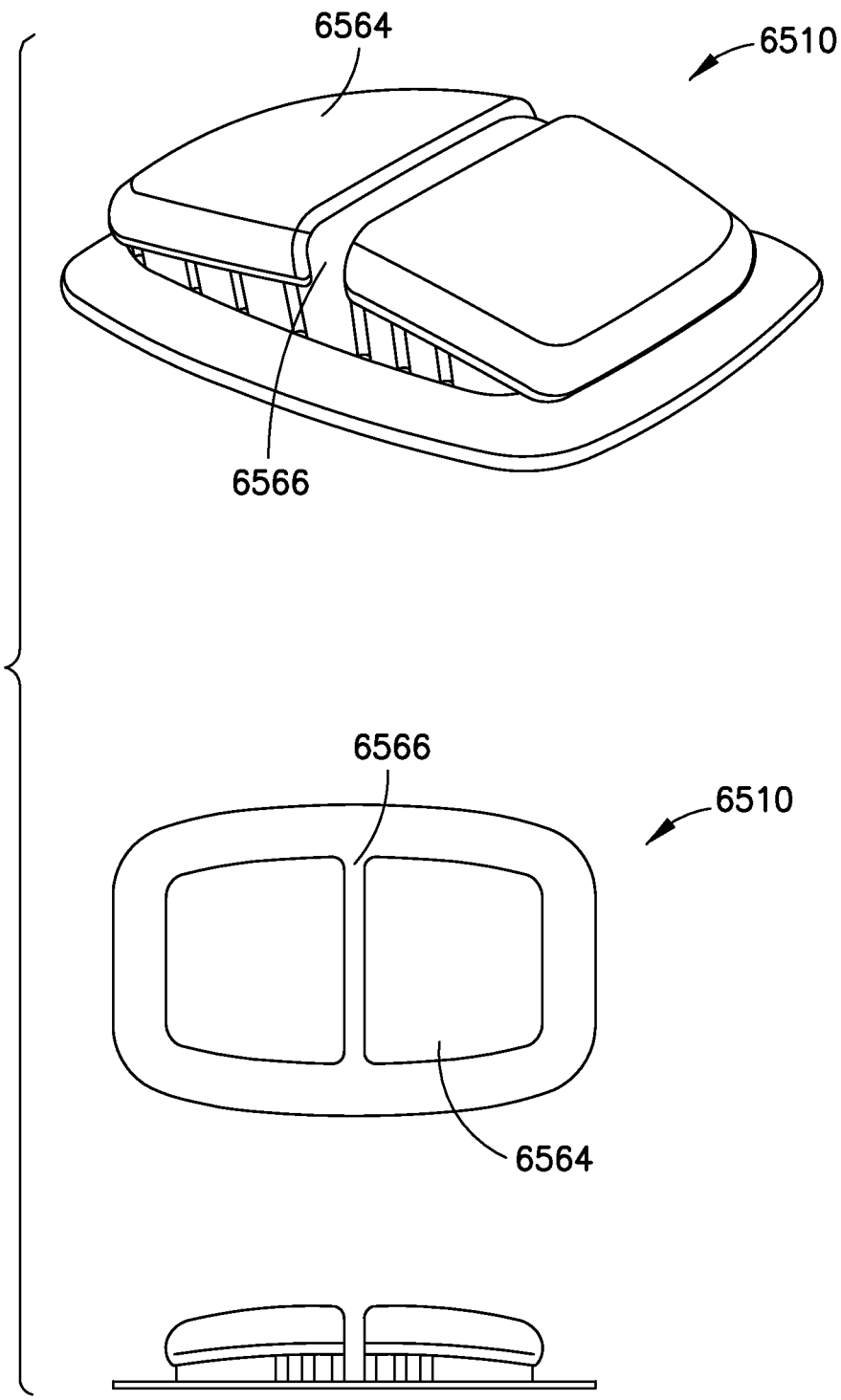
FIG. 65 shows another illustrative embodiment of an OBS device in accordance with the present invention, having sloped top surfaces and a center flex zone.

FIG. 65 shows an illustrative embodiment of an OBS 6510 having sloped top surfaces 6564 and a center flex zone 6566 providing flexibility to the OBS 6510.

Figure 66:
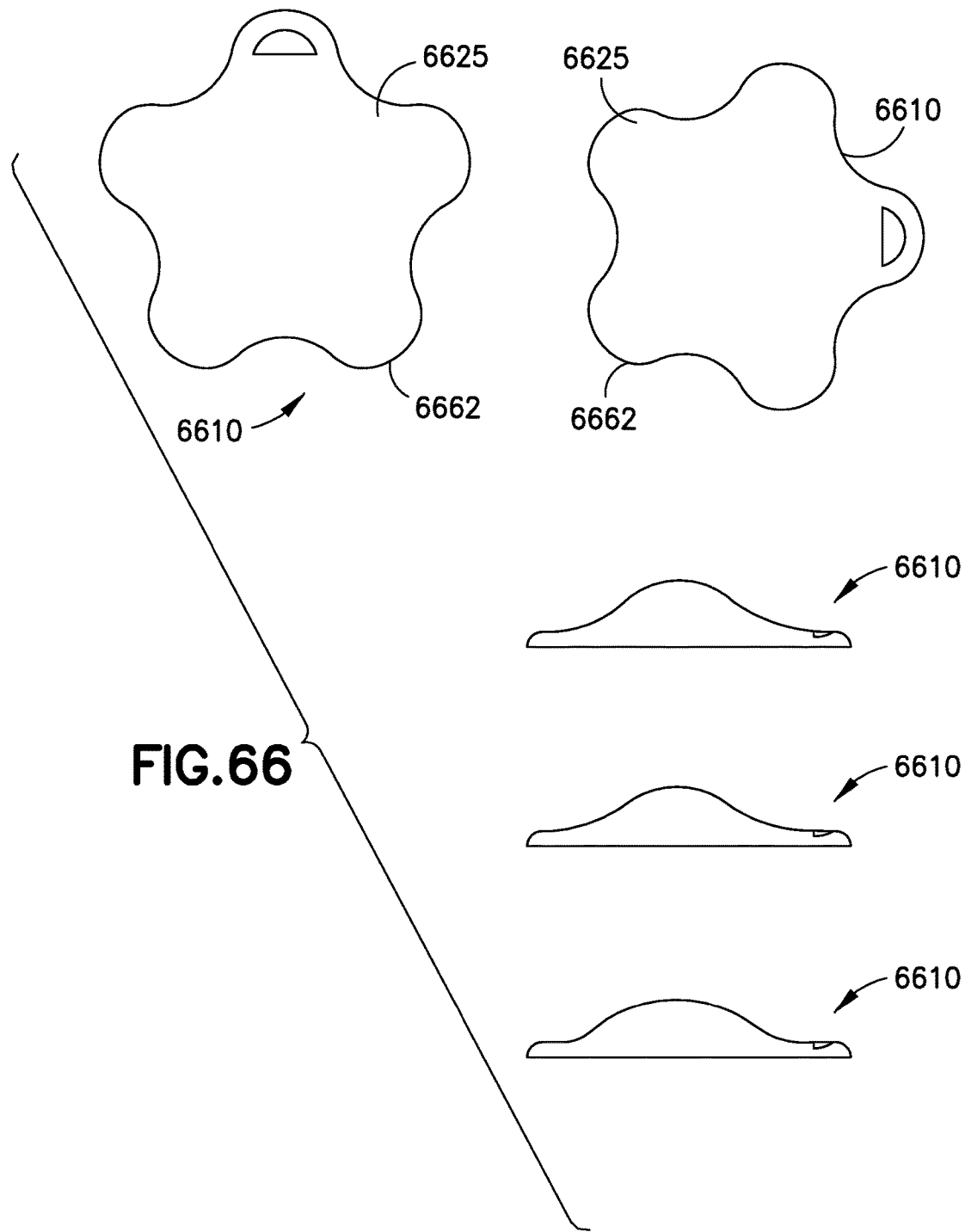
FIG. 66 shows another illustrative embodiment of an OBS device in accordance with the present invention, having a unitary cover with a plurality of rounded extensions.

FIG. 66 shows an illustrative embodiment of an OBS 6610 including a unitary cover 6625 having a plurality of rounded extensions 6662 around the perimeter of the OBS 6610.

Figure 67:
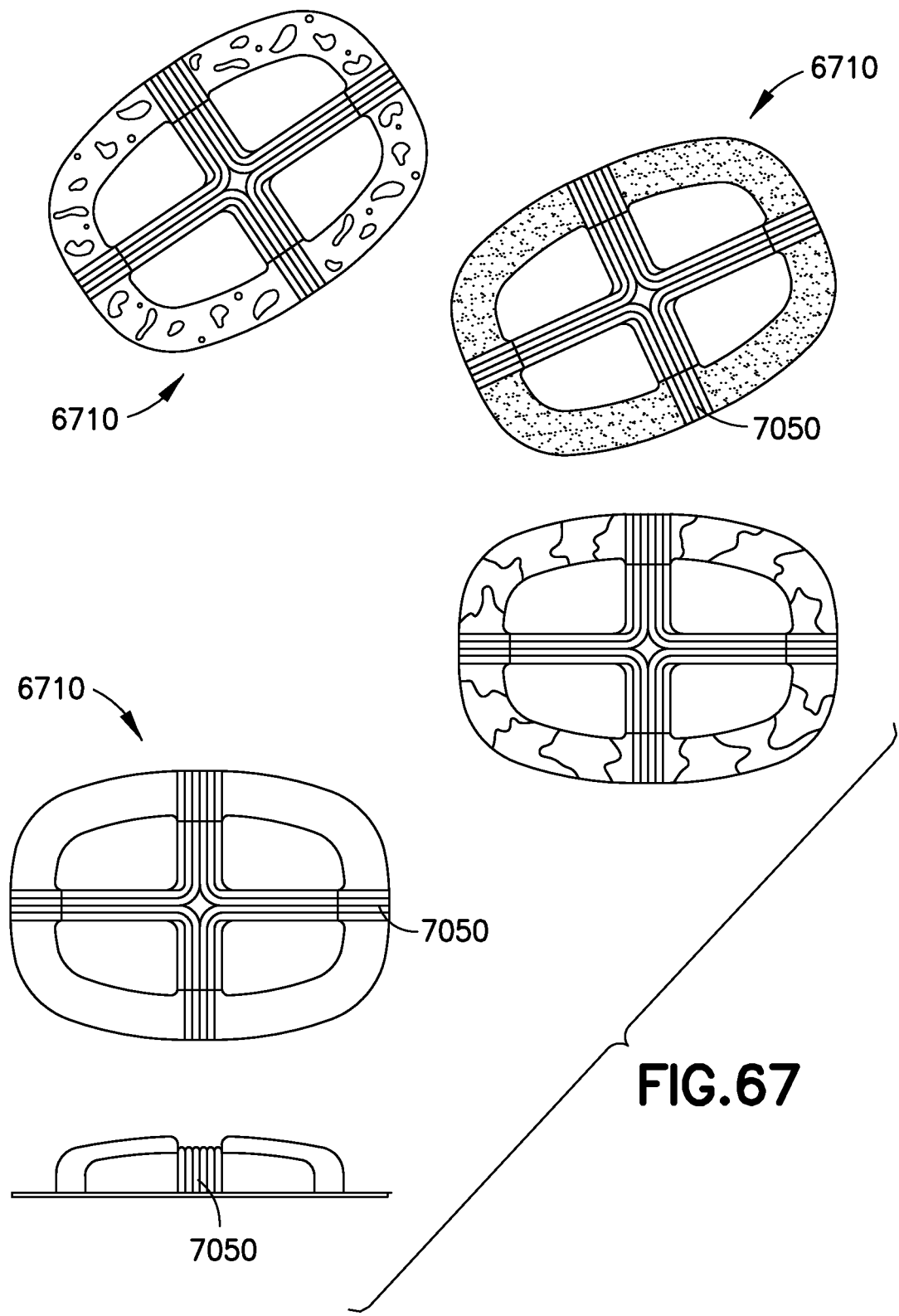
FIG. 67 shows another illustrative embodiment of an OBS device in accordance with the present invention, having textured recess portions.

FIG. 67 shows an illustrative embodiment of an OBS 6700 having textured recess portions 7050 which improves the handling of the OBS during application and removal.

Although only a few illustrative embodiments of the present invention have been described in detail above, those skilled in the art will readily appreciate that many modifications are possible in the illustrative embodiments, and various combinations of the illustrative embodiments are possible, without materially departing from the novel teachings and advantages of this invention. Accordingly, all such modifications are intended to be included within the scope of this invention.

The invention claimed is:

1. An on-body device for sensing an analyte in a living body, comprising:
 a cover at least partially containing a glucose monitoring sensor; and
 a first bottom surface adapted to be adhered to skin, further adapted to reduce at least one of skin irritation and nuisance to a user, and
 further comprising a telescoping stabilizer securable to a user and adapted to act as a guide during a needle insertion.

2. The on-body device of claim 1, further comprising a handle adapted to force the cover in a direction of a user.

3. The on-body device of claim 2, wherein the handle is removable.

4. The on-body device of claim 2, wherein the handle is made of a fabric material.

5. The on-body device of claim 2, wherein the handle has a substantially narrow and elongated shape, and wherein the cover is formed by silicone.

6. The on-body device of claim 2, wherein the cover and the handle have an hourglass-like shape.

7. The on-body device of claim 1, wherein the first bottom surface comprises a first adhesive.

8. The on-body device of claim 7, further comprising a first adhesive release paper that can be removed to expose the first adhesive.

9. The on-body device of claim 8, first adhesive release paper comprises opposing flaps that are adapted to be joined together above the cover.

10. The on-body device of claim 1, further comprising a handle hinged to a top surface of the cover.

11. The on-body device of claim 10, wherein the handle is adapted to be rotated to a substantially parallel position with respect to a top surface of the cover.

12. The on-body device of claim 1, wherein the telescoping stabilizer is received into a body of the cover during the needle insertion.

13. The on-body device of claim 1, wherein the cover comprises cutout portions adapted to enable independent flexibility of a perimeter of the cover.

14. The on-body device of claim 1, further comprising a knob adapted to aid in inserting and removing a needle.

15. The on-body device of claim 1, further comprising a window adapted to enable a use to visually inspect a continuous a device within the cover.

16. The on-body device of claim 1, further comprising a battery pod to house a battery.

17. The on-body device of claim 1, further comprising scooped sides.

18. The on-body device of claim 17, further comprising exposed elastomer.

19. The on-body device of claim 1, further comprising a fabric bandage material adhesive.

20. The on-body device of claim 1, further comprising a removable foam layer.

21. The on-body device of claim 1, further comprising flat adhesive petals around a perimeter of the on-body device.

22. The on-body device of claim 1, further comprising a needle inserter colored to match the cover.

23. The on-body device of claim 1, comprising a lanyard-style handle.

24. The on-body device of claim 1, comprising a recessed center portion.

25. The on-body device of claim 1, further comprising flex zones adapted to flex the on-body device and conform to the user.

26. The on-body device of claim 1, further comprising sloped top surfaces and a center flex zone.

27. The on-body device of claim 1, wherein the on-body device has a gradual reduced thickness from a central position out to a peripheral position.

28. The on-body device of claim 1, wherein the on-body device is substantially diamond-shaped.

29. The on-body device of claim 1, wherein the on-body device has a domed ellipse shape.

30. The on-body device of claim 1, wherein the on-body device has a substantially hourglass shape.

31. The on-body device of claim 1, wherein the on-body device has an annular shape.

32. The on-body device of claim 1, wherein the on-body device has a smooth radial exterior surface.

33. The on-body device of claim 1, wherein the on-body device has subtle curved outer edges.

34. The on-body device of claim 1, further comprising textured recess portions adapted to improve a handling of the on-body device during application and removal.

35. The on-body device of claim 1, further comprising a slight compound curved adhesive surface.

36. The on-body device of claim 1, wherein the cover comprises an overlapping square design.

37. The on-body device of claim 1, wherein the cover comprises having a fading grip pattern design.

38. The on-body device of claim 1, wherein the cover comprises a knit pattern design.

39. The on-body device of claim 1, wherein the cover comprises a lattice design.

40. The on-body device of claim 1, wherein the cover comprises having a random dots pattern.

41. The on-body device of claim 1, wherein the cover comprises is mounted on a foam layer ring.

42. The on-body device of claim 1, wherein the cover comprises a recessed portion adapted to receive a needle inserter assembly.

43. The on-body device of claim 42, wherein the needle inserter assembly comprises a second adhesive.

44. The on-body device of claim 43, further comprising a second adhesive release paper that can be removed to expose the second adhesive.

45. The on-body device of claim 1, wherein the cover is formed from a semi-flexible material.

46. The on-body device of claim 1, wherein the cover is formed of a foam-like material.

47. The on-body device of claim 1, wherein the cover is sloped and flexible.

48. The on-body device of claim 1, wherein the cover has elastomer nodules adapted to provide grip during handling.

49. The on-body device of claim 1, wherein the cover is unitary, soft and flexible.

50. The on-body device of claim 1, wherein the cover is unitary and comprises a plurality of rounded extensions around the perimeter of the on-body device.

51. The on-body device of claim 1, wherein the cover has a substantially pinwheel shape.

52. The on-body device of claim 1, wherein the cover is adapted to receive a stabilizer having telescoping pins.

53. The on-body device of claim 1, wherein the cover has a profile of substantially 8 millimeters.

54. The on-body device of claim 1, wherein the cover has a profile of substantially 10 millimeters.

55. An on-body device for sensing an analyte in a living body, comprising:
a cover at least partially containing a glucose monitoring sensor; and
a first bottom surface adapted to be adhered to skin, and further adapted to reduce at least one of skin irritation and nuisance to a user;
wherein the cover is adapted to receive a stabilizer having a rotating sleeve adapted to enable the cover to rotate with respect to the stabilizer during needle insertion.

56. An on-body device for sensing an analyte in a living body, comprising:
a cover at least partially containing a glucose monitoring sensor; and
a first bottom surface adapted to be adhered to skin, and further adapted to reduce at least one of skin irritation and nuisance to a user;
wherein the cover comprises a hinged handle and a pull cord adapted to be pulled to separate the on-body device from a user after use.

57. An on-body device for sensing an analyte in a living body, comprising:
a cover at least partially containing a glucose monitoring sensor; and
a first bottom surface adapted to be adhered to skin, and further adapted to reduce at least one of skin irritation and nuisance to a user; and
further comprising a flange; and
further comprising a handle, and wherein the handle can be broken off and separated from the cover and stowed in a recess between the cover and the flange.

58. The on-body device of claim 57, wherein the flange slopes down from the cover to an outer perimeter of the flange.

59. The on-body device of claim 57, wherein the flange is substantially triangular.

60. The on-body device of claim 57, further comprising a recess formed between the cover and the flange, wherein the recess provides a handle portion.

61. The on-body device of claim 57, further comprising a rotatable handle portion rotatable respect to the flange.

62. The on-body device of claim 57, wherein the flange comprises a compound curved-shaped flange.

63. The on-body device of claim 57, wherein the flange comprises a convex flange or a concave flange.

64. The on-body device of claim 57, wherein the flange comprises a pinwheel-shaped flange.

65. The on-body device of claim 57, wherein the flange has a slightly asymmetrical shape and comprises a removal tape on a bottom surface of the flange.

66. The on-body device of claim 57, wherein the flange has a slightly higher profile than the cover.

67. The on-body device of claim 57, wherein the flange is slightly elongated and stop, and wherein the cover is square-shaped.

68. The on-body device of claim 57, wherein a top surface of the flange comprises elastomeric bumps.

\* \* \* \* \*